US012064280B2

(12) United States Patent
Kedmi-Shahar et al.

(10) Patent No.: US 12,064,280 B2
(45) Date of Patent: *Aug. 20, 2024

(54) SYSTEM AND METHOD FOR IDENTIFYING AND MARKING A TARGET IN A FLUOROSCOPIC THREE-DIMENSIONAL RECONSTRUCTION

(71) Applicant: Covidien LP, Mansfield, MA (US)

(72) Inventors: Efrat Kedmi-Shahar, Pardesia (IL); Dafna Mardix, Herzliya (IL); Evgeni Kopel, Barkan (IL); Oren P. Weingarten, Hod-Hasharon (IL); Benjamin Greenburg, Hod Hasharon (IL); Eyal Klein, Tel Aviv (IL); Ron Barak, Tel Aviv (IL)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/104,164

(22) Filed: Jan. 31, 2023

(65) Prior Publication Data
US 2023/0172574 A1 Jun. 8, 2023

Related U.S. Application Data

(63) Continuation of application No. 17/115,599, filed on Dec. 8, 2020, now Pat. No. 11,564,649, which is a
(Continued)

(51) Int. Cl.
*A61B 6/00* (2024.01)
*A61B 6/03* (2006.01)
(Continued)

(52) U.S. Cl.
CPC ............ *A61B 6/5205* (2013.01); *A61B 6/032* (2013.01); *A61B 6/12* (2013.01); *A61B 6/463* (2013.01);
(Continued)

(58) Field of Classification Search
CPC .............. G06V 10/24; G06V 2201/034; G06T 2207/10121; G06T 2210/41;
(Continued)

(56) References Cited

U.S. PATENT DOCUMENTS 5,057,494 A 10/1991 Sheffield
5,321,113 A 6/1994 Cooper et al.
(Continued)

FOREIGN PATENT DOCUMENTS

BR 0013237 A 7/2003
BR 0116004 A 6/2004
(Continued)

OTHER PUBLICATIONS

Australian Examination Report No. 2 issued in Appl. No. AU 2016210747 dated Oct. 18, 2017 (4 pages).
(Continued)

*Primary Examiner* — Guillermo M Rivera-Martinez
(74) *Attorney, Agent, or Firm* — Weber Rosselli & Cannon LLP

(57) ABSTRACT

A method and system for facilitating identification and marking of a target in a displayed Fluoroscopic Three-Dimensional Reconstruction (F3DR) of a body region of a patient. The system includes a display and a storage device storing instructions for receiving an initial selection of the target in the F3DR, fining the F3DR based on the initial selection of the target, displaying the fined F3DR on the display, and receiving a final selection of the target in the fined F3DR via a user selection. The system further includes at least one hardware processor configured to execute said instructions. The method and instructions may also include receiving a selection of a medical device in two two-dimensional fluoroscopic images, where the medical device
(Continued)

is located in an area of the target, and initially fining the F3DR based on the selection of the medical device.

20 Claims, 14 Drawing Sheets

Related U.S. Application Data continuation of application No. 16/156,650, filed on Oct. 10, 2018, now Pat. No. 10,893,843.

(60) Provisional application No. 62/641,777, filed on Mar. 12, 2018, provisional application No. 62/628,017, filed on Feb. 8, 2018, provisional application No. 62/570,431, filed on Oct. 10, 2017.

(51) Int. Cl.
| | | |
|---|---|---|
| *A61B 6/12* | (2006.01) | |
| *A61B 6/46* | (2024.01) | |
| *A61B 34/00* | (2016.01) | |
| *A61B 90/00* | (2016.01) | |
| *G06T 11/00* | (2006.01) | |

(52) U.S. Cl.
CPC ............ *A61B 6/487* (2013.01); *A61B 6/488* (2013.01); *A61B 34/25* (2016.02); *A61B 90/39* (2016.02); *G06T 11/003* (2013.01); *A61B 2034/252* (2016.02); *A61B 2090/367* (2016.02); *A61B 2090/376* (2016.02); *A61B 2090/3908* (2016.02)

(58) Field of Classification Search
CPC . G06T 2207/10124; G06T 2207/30004; G06T 2207/10072
See application file for complete search history.

(56) References Cited

U.S. PATENT DOCUMENTS

| | | |
|---|---|---|
| 5,706,324 A | 1/1998 | Wiesent et al. |
| 5,852,646 A | 12/1998 | Klotz et al. |
| 5,930,329 A | 7/1999 | Navab |
| 5,951,475 A | 9/1999 | Gueziec et al. |
| 5,963,612 A | 10/1999 | Navab |
| 5,963,613 A | 10/1999 | Navab |
| 6,003,517 A | 12/1999 | Sheffield et al. |
| 6,038,282 A | 3/2000 | Wiesent et al. |
| 6,049,582 A | 4/2000 | Navab |
| 6,050,724 A | 4/2000 | Schmitz et al. |
| 6,055,449 A | 4/2000 | Navab |
| 6,081,577 A | 6/2000 | Webber |
| 6,118,845 A | 9/2000 | Simon et al. |
| 6,120,180 A | 9/2000 | Graumann |
| 6,236,704 B1 | 5/2001 | Navab et al. |
| 6,243,439 B1 | 6/2001 | Arai et al. |
| 6,285,739 B1 | 9/2001 | Rudin et al. |
| 6,289,235 B1 | 9/2001 | Webber et al. |
| 6,317,621 B1 | 11/2001 | Graumann et al. |
| 6,351,513 B1 | 2/2002 | Bani-Hashemi et al. |
| 6,359,960 B1 | 3/2002 | Wahl et al. |
| 6,373,916 B1 | 4/2002 | Inoue et al. |
| 6,382,835 B2 | 5/2002 | Graumann et al. |
| 6,389,104 B1 | 5/2002 | Bani-Hashemi et al. |
| 6,404,843 B1 | 6/2002 | Vaillant |
| 6,424,731 B1 | 7/2002 | Launay et al. |
| 6,473,634 B1 | 10/2002 | Barni |
| 6,484,049 B1 | 11/2002 | Seeley et al. |
| 6,485,422 B1 | 11/2002 | Mikus et al. |
| 6,490,475 B1 | 12/2002 | Seeley et al. |
| 6,491,430 B1 | 12/2002 | Seissler |
| 6,493,575 B1 | 12/2002 | Kesten et al. |
| 6,546,068 B1 | 4/2003 | Shimura |
| 6,546,279 B1 | 4/2003 | Bova et al. |
| 6,549,607 B1 | 4/2003 | Webber |
| 6,585,412 B2 | 7/2003 | Mitschke |
| 6,662,036 B2 | 12/2003 | Cosman |
| 6,666,579 B2 | 12/2003 | Jensen |
| 6,697,664 B2 | 2/2004 | Kienzle et al. |
| 6,707,878 B2 | 3/2004 | Claus et al. |
| 6,714,810 B2 | 3/2004 | Grzeszczuk et al. |
| 6,731,283 B1 | 5/2004 | Navab |
| 6,731,970 B2 | 5/2004 | Schlossbauer et al. |
| 6,768,784 B1 | 7/2004 | Green et al. |
| 6,782,287 B2 | 8/2004 | Grzeszczuk et al. |
| 6,785,356 B2 | 8/2004 | Grass et al. |
| 6,785,571 B2 | 8/2004 | Glossop |
| 6,801,597 B2 | 10/2004 | Webber |
| 6,810,278 B2 | 10/2004 | Webber et al. |
| 6,823,207 B1 | 11/2004 | Jensen et al. |
| 6,851,855 B2 | 2/2005 | Mitschke et al. |
| 6,856,826 B2 | 2/2005 | Seeley et al. |
| 6,856,827 B2 | 2/2005 | Seeley et al. |
| 6,865,253 B2 | 3/2005 | Blumhofer et al. |
| 6,898,263 B2 | 5/2005 | Avinash et al. |
| 6,912,265 B2 | 6/2005 | Hebecker et al. |
| 6,928,142 B2 | 8/2005 | Shao et al. |
| 6,944,260 B2 | 9/2005 | Hsieh et al. |
| 6,956,927 B2 | 10/2005 | Sukeyasu et al. |
| 7,010,080 B2 | 3/2006 | Mitschke et al. |
| 7,010,152 B2 | 3/2006 | Bojer et al. |
| 7,035,371 B2 | 4/2006 | Boese et al. |
| 7,048,440 B2 | 5/2006 | Graumann et al. |
| 7,066,646 B2 | 6/2006 | Pescatore et al. |
| 7,106,825 B2 | 9/2006 | Gregerson et al. |
| 7,117,027 B2 | 10/2006 | Zheng et al. |
| 7,129,946 B2 | 10/2006 | Ditt et al. |
| 7,130,676 B2 | 10/2006 | Barrick |
| 7,142,633 B2 | 11/2006 | Eberhard et al. |
| 7,147,373 B2 | 12/2006 | Cho et al. |
| 7,165,362 B2 | 1/2007 | Jobs et al. |
| 7,186,023 B2 | 3/2007 | Morita et al. |
| 7,251,522 B2 | 7/2007 | Essenreiter et al. |
| 7,327,872 B2 | 2/2008 | Vaillant et al. |
| 7,343,195 B2 | 3/2008 | Strommer et al. |
| 7,369,641 B2 | 5/2008 | Tsubaki et al. |
| 7,426,256 B2 | 9/2008 | Rasche et al. |
| 7,440,538 B2 | 10/2008 | Tsujii |
| 7,467,007 B2 | 12/2008 | Othert |
| 7,474,913 B2 | 1/2009 | Durlak |
| 7,502,503 B2 | 3/2009 | Bojer et al. |
| 7,505,549 B2 | 3/2009 | Ohishi et al. |
| 7,508,388 B2 | 3/2009 | Barfuss et al. |
| 7,551,759 B2 | 6/2009 | Hristov et al. |
| 7,603,155 B2 | 10/2009 | Jensen et al. |
| 7,620,223 B2 | 11/2009 | Xu et al. |
| 7,639,866 B2 | 12/2009 | Pomero et al. |
| 7,664,542 B2 | 2/2010 | Boese et al. |
| 7,671,887 B2 | 3/2010 | Pescatore et al. |
| 7,689,019 B2 | 3/2010 | Boese et al. |
| 7,689,042 B2 | 3/2010 | Brunner et al. |
| 7,693,263 B2 | 4/2010 | Bouvier et al. |
| 7,711,082 B2 | 5/2010 | Fujimoto et al. |
| 7,711,083 B2 | 5/2010 | Heigl et al. |
| 7,711,409 B2 | 5/2010 | Keppel et al. |
| 7,712,961 B2 | 5/2010 | Horndler et al. |
| 7,720,520 B2 | 5/2010 | Willis |
| 7,725,165 B2 | 5/2010 | Chen et al. |
| 7,734,329 B2 | 6/2010 | Boese et al. |
| 7,742,557 B2 | 6/2010 | Brunner et al. |
| 7,761,135 B2 | 7/2010 | Pfister et al. |
| 7,778,685 B2 | 8/2010 | Evron et al. |
| 7,778,690 B2 | 8/2010 | Boese et al. |
| 7,787,932 B2 | 8/2010 | Vilsmeier et al. |
| 7,804,991 B2 | 9/2010 | Abovitz et al. |
| 7,831,096 B2 | 11/2010 | Williamson et al. |
| 7,835,779 B2 | 11/2010 | Anderson et al. |
| 7,844,094 B2 | 11/2010 | Jeung et al. |
| 7,853,061 B2 | 12/2010 | Gorges et al. |
| 7,877,132 B2 | 1/2011 | Rongen et al. |
| 7,899,226 B2 | 3/2011 | Pescatore et al. |
| 7,907,989 B2 | 3/2011 | Borgert et al. |
| 7,912,180 B2 | 3/2011 | Zou et al. |

(56) References Cited

U.S. PATENT DOCUMENTS

| | | |
|---|---|---|
| 7,912,262 B2 | 3/2011 | Timmer et al. |
| 7,916,918 B2 | 3/2011 | Suri et al. |
| 7,949,088 B2 | 5/2011 | Nishide et al. |
| 7,950,849 B2 | 5/2011 | Bernhard et al. |
| 7,991,450 B2 | 8/2011 | Virtue et al. |
| 8,000,436 B2 | 8/2011 | Seppi et al. |
| 8,043,003 B2 | 10/2011 | Vogt et al. |
| 8,045,780 B2 | 10/2011 | Boese et al. |
| 8,050,739 B2 | 11/2011 | Eck et al. |
| 8,090,168 B2 | 1/2012 | Washburn et al. |
| 8,104,958 B2 | 1/2012 | Weiser et al. |
| 8,111,894 B2 | 2/2012 | Haar |
| 8,111,895 B2 | 2/2012 | Spahn |
| 8,126,111 B2 | 2/2012 | Uhde et al. |
| 8,126,241 B2 | 2/2012 | Zarkh et al. |
| 8,150,131 B2 | 4/2012 | Harer et al. |
| 8,180,132 B2 | 5/2012 | Gorges et al. |
| 8,195,271 B2 | 6/2012 | Rahn |
| 8,200,316 B2 | 6/2012 | Keppel et al. |
| 8,208,708 B2 | 6/2012 | Homan et al. |
| 8,229,061 B2 | 7/2012 | Hanke et al. |
| 8,248,413 B2 | 8/2012 | Gattani et al. |
| 8,270,691 B2 | 9/2012 | Xu et al. |
| 8,271,068 B2 | 9/2012 | Khamene et al. |
| 8,275,448 B2 | 9/2012 | Camus et al. |
| 8,306,303 B2 | 11/2012 | Bruder et al. |
| 8,311,617 B2 | 11/2012 | Keppel et al. |
| 8,320,992 B2 | 11/2012 | Frenkel et al. |
| 8,326,403 B2 | 12/2012 | Pescatore et al. |
| 8,335,359 B2 | 12/2012 | Fidrich et al. |
| 8,340,379 B2 | 12/2012 | Razzaque et al. |
| 8,345,817 B2 | 1/2013 | Fuchs et al. |
| 8,374,416 B2 | 2/2013 | Gagesch et al. |
| 8,374,678 B2 | 2/2013 | Graumann |
| 8,423,117 B2 | 4/2013 | Pichon et al. |
| 8,442,618 B2 | 5/2013 | Strommer et al. |
| 8,482,606 B2 | 7/2013 | Razzaque et al. |
| 8,515,527 B2 | 8/2013 | Vaillant et al. |
| 8,526,688 B2 | 9/2013 | Groszmann et al. |
| 8,526,700 B2 | 9/2013 | Isaacs |
| 8,532,258 B2 | 9/2013 | Bulitta et al. |
| 8,532,259 B2 | 9/2013 | Shedlock et al. |
| 8,548,567 B2 | 10/2013 | Maschke et al. |
| 8,625,869 B2 | 1/2014 | Harder et al. |
| 8,666,137 B2 | 3/2014 | Nielsen et al. |
| 8,670,603 B2 | 3/2014 | Tolkowsky et al. |
| 8,675,996 B2 | 3/2014 | Liao et al. |
| 8,693,622 B2 | 4/2014 | Graumann et al. |
| 8,693,756 B2 | 4/2014 | Tolkowsky et al. |
| 8,694,075 B2 | 4/2014 | Groszmann et al. |
| 8,706,184 B2 | 4/2014 | Mohr et al. |
| 8,706,186 B2 | 4/2014 | Fichtinger et al. |
| 8,712,129 B2 | 4/2014 | Strommer et al. |
| 8,718,346 B2 | 5/2014 | Isaacs et al. |
| 8,750,582 B2 | 6/2014 | Boese et al. |
| 8,755,587 B2 | 6/2014 | Bender et al. |
| 8,781,064 B2 | 7/2014 | Fuchs et al. |
| 8,792,704 B2 | 7/2014 | Isaacs |
| 8,798,339 B2 | 8/2014 | Mielekamp et al. |
| 8,827,934 B2 | 9/2014 | Chopra et al. |
| 8,831,310 B2 | 9/2014 | Razzaque et al. |
| 8,855,748 B2 | 10/2014 | Keppel et al. |
| 9,001,121 B2 | 4/2015 | Finlayson et al. |
| 9,001,962 B2 | 4/2015 | Funk |
| 9,008,367 B2 | 4/2015 | Tolkowsky et al. |
| 9,031,188 B2 | 5/2015 | Belcher et al. |
| 9,036,777 B2 | 5/2015 | Ohishi et al. |
| 9,042,624 B2 | 5/2015 | Dennerlein |
| 9,044,190 B2 | 6/2015 | Rubner et al. |
| 9,087,404 B2 | 7/2015 | Hansis et al. |
| 9,095,252 B2 | 8/2015 | Popovic |
| 9,104,902 B2 | 8/2015 | Xu et al. |
| 9,111,175 B2 | 8/2015 | Strommer et al. |
| 9,135,706 B2 | 9/2015 | Zagorchev et al. |
| 9,171,365 B2 | 10/2015 | Mareachen et al. |
| 9,179,878 B2 | 11/2015 | Jeon |
| 9,216,065 B2 | 12/2015 | Cohen et al. |
| 9,232,924 B2 | 1/2016 | Liu et al. |
| 9,262,830 B2 | 2/2016 | Bakker et al. |
| 9,265,468 B2 | 2/2016 | Rai et al. |
| 9,277,893 B2 | 3/2016 | Tsukagoshi et al. |
| 9,280,837 B2 | 3/2016 | Grass et al. |
| 9,282,944 B2 | 3/2016 | Fallavollita et al. |
| 9,375,268 B2 | 6/2016 | Long |
| 9,401,047 B2 | 7/2016 | Bogoni et al. |
| 9,406,134 B2 | 8/2016 | Klingenbeck-Regn et al. |
| 9,433,390 B2 | 9/2016 | Nathaniel et al. |
| 9,445,772 B2 | 9/2016 | Callaghan et al. |
| 9,445,776 B2 | 9/2016 | Han et al. |
| 9,466,135 B2 | 10/2016 | Koehler et al. |
| 9,743,896 B2 | 8/2017 | Averbuch |
| 9,833,167 B2 | 12/2017 | Cohen et al. |
| 9,888,898 B2 | 2/2018 | Imagawa et al. |
| 9,918,659 B2 | 3/2018 | Chopra et al. |
| 10,004,558 B2 | 6/2018 | Long et al. |
| 10,127,629 B2 | 11/2018 | Razzaque et al. |
| 10,130,316 B2 | 11/2018 | Funabasama et al. |
| 10,194,897 B2 | 2/2019 | Cedro et al. |
| 10,373,719 B2 | 8/2019 | Soper et al. |
| 10,376,178 B2 | 8/2019 | Chopra |
| 10,405,753 B2 | 9/2019 | Sorger |
| 10,478,162 B2 | 11/2019 | Barbagli et al. |
| 10,480,926 B2 | 11/2019 | Froggatt et al. |
| 10,524,866 B2 | 1/2020 | Srinivasan et al. |
| 10,555,788 B2 | 2/2020 | Panescu et al. |
| 10,569,071 B2 | 2/2020 | Harris et al. |
| 10,603,106 B2 | 3/2020 | Weide et al. |
| 10,610,306 B2 | 4/2020 | Chopra |
| 10,638,953 B2 | 5/2020 | Duindam et al. |
| 10,639,114 B2 | 5/2020 | Schuh et al. |
| 10,674,970 B2 | 6/2020 | Averbuch et al. |
| 10,682,070 B2 | 6/2020 | Duindam |
| 10,702,137 B2 | 7/2020 | Deyanov |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,885,630 B2 | 1/2021 | Li et al. |
| 10,896,506 B2 | 1/2021 | Zhao et al. |
| 2002/0122536 A1 | 9/2002 | Kerrien et al. |
| 2002/0147462 A1 | 10/2002 | Mair et al. |
| 2002/0163996 A1 | 11/2002 | Kerrien et al. |
| 2002/0188194 A1 | 12/2002 | Cosman |
| 2003/0013972 A1 | 1/2003 | Makin |
| 2003/0088179 A1 | 5/2003 | Seeley et al. |
| 2003/0095147 A1* | 5/2003 | Daw ............... G01R 33/56 715/771 |
| 2004/0120981 A1 | 6/2004 | Nathan |
| 2005/0220264 A1 | 10/2005 | Homegger |
| 2005/0245807 A1 | 11/2005 | Boese et al. |
| 2005/0281385 A1 | 12/2005 | Johnson et al. |
| 2006/0182216 A1 | 8/2006 | Lauritsch et al. |
| 2006/0251213 A1 | 11/2006 | Bernhardt et al. |
| 2007/0100234 A1* | 5/2007 | Arenson ............. A61B 6/032 600/429 |
| 2007/0276216 A1 | 11/2007 | Beyar et al. |
| 2008/0045938 A1 | 2/2008 | Weide et al. |
| 2008/0049014 A1* | 2/2008 | Haimerl ............. G06T 7/80 345/419 |
| 2009/0080765 A1 | 3/2009 | Bernard et al. |
| 2009/0163800 A1 | 6/2009 | Xu et al. |
| 2013/0231556 A1* | 9/2013 | Holsing ........... A61B 10/0283 600/424 |
| 2013/0303945 A1 | 11/2013 | Blumenkranz et al. |
| 2014/0035798 A1 | 2/2014 | Kawada et al. |
| 2014/0046175 A1 | 2/2014 | Ladtkow et al. |
| 2014/0232840 A1* | 8/2014 | Holsing ............. A61B 1/0005 348/65 |
| 2014/0281961 A1* | 9/2014 | Baker ............... G16H 30/40 715/705 |
| 2014/0343408 A1 | 11/2014 | Tolkowsky |

(56) References Cited

U.S. PATENT DOCUMENTS

| | | |
|---|---|---|
| 2015/0148690 A1 | 5/2015 | Chopra et al. |
| 2015/0223902 A1 | 8/2015 | Walker et al. |
| 2015/0227679 A1 | 8/2015 | Kamer et al. |
| 2015/0265368 A1 | 9/2015 | Chopra et al. |
| 2015/0320513 A1 | 11/2015 | Yoon et al. |
| 2015/0342546 A1* | 12/2015 | Zaiki ................ A61B 6/503 378/62 |
| 2016/0000302 A1* | 1/2016 | Brown ................ A61B 6/466 600/103 |
| 2016/0005194 A1 | 1/2016 | Schretter et al. |
| 2016/0120521 A1 | 5/2016 | Weingarten et al. |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0206380 A1 | 7/2016 | Sparks et al. |
| 2016/0287343 A1 | 10/2016 | Eichler et al. |
| 2016/0287344 A1 | 10/2016 | Donhowe et al. |
| 2016/0302747 A1 | 10/2016 | Averbuch |
| 2017/0035379 A1 | 2/2017 | Weingarten et al. |
| 2017/0035380 A1 | 2/2017 | Barak et al. |
| 2017/0112571 A1 | 4/2017 | Thiel et al. |
| 2017/0112576 A1 | 4/2017 | Coste-Maniere et al. |
| 2017/0151027 A1 | 6/2017 | Walker et al. |
| 2017/0209071 A1 | 7/2017 | Zhao et al. |
| 2017/0258526 A1* | 9/2017 | Lang ................ H05K 999/99 |
| 2017/0265952 A1 | 9/2017 | Donhowe et al. |
| 2017/0311844 A1 | 11/2017 | Zhao et al. |
| 2017/0319165 A1 | 11/2017 | Averbuch |
| 2018/0078318 A1 | 3/2018 | Barbagli et al. |
| 2018/0144092 A1 | 5/2018 | Flitsch et al. |
| 2018/0153621 A1 | 6/2018 | Duindam et al. |
| 2018/0160991 A1 | 6/2018 | Chun et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0310907 A1* | 11/2018 | Zhang ................ G06F 3/0346 |
| 2018/0325419 A1 | 11/2018 | Zhao et al. |
| 2019/0000559 A1 | 1/2019 | Berman et al. |
| 2019/0000560 A1 | 1/2019 | Berman et al. |
| 2019/0005687 A1 | 1/2019 | Weingarten et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0110839 A1 | 4/2019 | Rafii-Tari et al. |
| 2019/0142528 A1* | 5/2019 | Vertikov ................ A61B 34/20 600/424 |
| 2019/0175062 A1 | 6/2019 | Rafii-Tari et al. |
| 2019/0175799 A1 | 6/2019 | Hsu et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0269818 A1 | 9/2019 | Dhanaraj et al. |
| 2019/0269819 A1 | 9/2019 | Dhanaraj et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0054408 A1 | 2/2020 | Schuh et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078023 A1 | 3/2020 | Cedro et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138514 A1 | 5/2020 | Blumenkranz et al. |
| 2020/0138515 A1 | 5/2020 | Wong |
| 2020/0142013 A1 | 5/2020 | Wong |
| 2020/0155116 A1 | 5/2020 | Donhowe et al. |
| 2020/0155232 A1 | 5/2020 | Wong |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188021 A1 | 6/2020 | Wong et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |
| 2020/0383750 A1 | 12/2020 | Kemp et al. |
| 2021/0000524 A1 | 1/2021 | Barry et al. |
| 2021/0192759 A1* | 6/2021 | Lang ................ G06T 3/40 |

FOREIGN PATENT DOCUMENTS

| | | |
|---|---|---|
| BR | 0307259 A | 12/2004 |
| BR | 0412298 A2 | 9/2006 |
| BR | 112018003862 A2 | 10/2018 |
| CN | 101190149 A | 6/2008 |
| CZ | 1644519 | 12/2008 |
| CZ | 486540 B1 | 9/2016 |
| CZ | 2709512 B6 | 8/2017 |
| CZ | 2884879 B1 | 1/2020 |
| DE | 19919907 A1 | 11/2000 |
| DE | 69726415 T | 9/2004 |
| DE | 102004004620 A1 | 8/2005 |
| EP | 0917855 A1 | 5/1999 |
| EP | 1593343 A2 | 11/2005 |
| EP | 1644519 B1 | 12/2008 |
| EP | 2141497 A1 | 1/2010 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| EP | 3749239 A1 | 12/2020 |
| JP | 2005332397 A * | 12/2005 ................ G06T 3/00 |
| MX | PA03005028 A | 1/2004 |
| MX | PA03000137 A | 9/2004 |
| MX | PA03006874 A | 9/2004 |
| MX | 225663 B | 1/2005 |
| MX | 226292 B | 2/2005 |
| MX | PA03010507 A | 7/2005 |
| MX | PA05011725 A | 5/2006 |
| MX | 06011286 | 3/2007 |

(56) References Cited

FOREIGN PATENT DOCUMENTS

| MX | 246862 B | 6/2007 |
|---|---|---|
| MX | 2007006441 A | 8/2007 |
| MX | 265247 B | 3/2009 |
| MX | 284569 B | 3/2011 |
| WO | 9944503 A1 | 9/1999 |
| WO | 0187136 A2 | 11/2001 |
| WO | 2004081877 A1 | 9/2004 |
| WO | 2005015125 A1 | 2/2005 |
| WO | 2005082246 A1 | 9/2005 |
| WO | 2009081297 A2 | 7/2009 |
| WO | 2015101948 A2 | 7/2015 |

OTHER PUBLICATIONS

Canadian Office Action issued in Appl. No. 2,937,825 dated Mar. 26, 2018 (4 pages).

Chinese Office Action issued in Chinese Patent Application No. 201880063882.2 dated Feb. 8, 2023. English translation not available.

CT scan—Wikipedia, the free encyclopedia [retrieved from internet on Mar. 30, 2017]. published on Jun. 30, 2015 as per Wayback Machine.

Office Action issued in Chinese Appl. No. 201610635896.X dated Jul. 23, 2018, together with English language translation (16 pages).

Steenbeke Femke et al: "Analysis of the targeting uncertainty of a stereotactic frameless radiosurgery technique for arteriovenous malformation; incl. Supplementary data" Radiotherapy and Oncology, Elsevier, Ireland, vol. 113, No. 3, Dec. 1, 2014 (Dec. 1, 2014), pp. 371-373.

\* cited by examiner

SYSTEM AND METHOD FOR IDENTIFYING AND MARKING A TARGET IN A FLUOROSCOPIC THREE-DIMENSIONAL RECONSTRUCTION

CROSS-REFERENCE TO RELATED APPLICATIONS

This application is a continuation of U.S. patent application Ser. No. 17/115,599 filed Dec. 12, 2020, which is a continuation of U.S. Pat. No. 10,893,843 filed Oct. 10, 2018, which claims the benefit of the filing dates of provisional U.S. Patent Application No. 62/570,431, filed Oct. 10, 2017, provisional U.S. Patent Application No. 62/641,777, filed Mar. 12, 2018, and provisional U.S. Patent Application No. 62/628,017, filed Feb. 8, 2018, the entire contents of each of which are incorporated herein by reference.

BACKGROUND

Technical Field

The present disclosure relates to the field of identifying and marking a target, such as a lesion or a small soft tissue object) in fluoroscopic images, 3D fluoroscopic images, fluoroscopic 3D reconstructions, or other data sets, in general, and to such target identification and marking in medical procedures involving intra-body navigation, in particular. Furthermore, the present disclosure relates to a system, apparatus, and methods of planning, navigating, identifying, marking, dying, biopsy, ablation, laparoscopy, or treatment in medical procedures.

Description of Related Art

There are several commonly applied medical methods, such as endoscopic procedures or minimally invasive procedures, for treating various maladies affecting organs including the liver, brain, heart, lung, gallbladder, kidney and bones. Often, one or more imaging modalities, such as magnetic resonance imaging (MRI), ultrasound imaging, computed tomography (CT), fluoroscopy as well as others are employed by clinicians to identify and navigate to areas of interest within a patient and ultimately a target for treatment. In some procedures, pre-operative scans may be utilized for target identification and intraoperative guidance. However, real-time imaging may be often required to obtain a more accurate and current image of the target area. Furthermore, real-time image data displaying the current location of a medical device with respect to the target and its surrounding may be required to navigate the medical device to the target in a more safe and accurate manner (e.g., with unnecessary or no damage caused to other organs or tissue).

For example, an endoscopic approach has proven useful in navigating to areas of interest within a patient, and particularly so for areas within luminal networks of the body such as the lungs. To enable the endoscopic approach, and more particularly the bronchoscopic approach in the lungs, endobronchial navigation systems have been developed that use previously acquired MRI data or CT image data to generate a three-dimensional (3D) rendering, model or volume of the particular body part such as the lungs.

The resulting volume generated from the MRI scan or CT scan is then utilized to create a navigation plan to facilitate the advancement of a navigation catheter (or other suitable medical device) through a bronchoscope and a branch of the bronchus of a patient to an area of interest. A locating or tracking system, such as an electromagnetic (EM) tracking system, may be utilized in conjunction with, for example, CT data, to facilitate guidance of the navigation catheter through the branch of the bronchus to the area of interest. In certain instances, the navigation catheter may be positioned within one of the airways of the branched luminal networks adjacent to, or within, the area of interest to provide access for one or more medical instruments.

However, a 3D volume of a patient's lungs, generated from previously acquired scans, such as CT scans, may not provide a basis sufficient for accurate guiding of medical instruments to a target during a navigation procedure. In certain instances, the inaccuracy is caused by deformation of the patient's lungs during the procedure relative to the lungs at the time of the acquisition of the previously acquired CT data. This deformation (CT-to-Body divergence) may be caused by many different factors including, for example, sedation vs. no sedation, bronchoscope changing patient pose and also pushing the tissue, different lung volume because CT was during inhale while navigation is during breathing, different bed, different day, etc.

Thus, another imaging modality is necessary to visualize such targets in real-time and enhance the in-vivo navigation procedure by correcting navigation during the procedure. Furthermore, in order to accurately and safely navigate medical devices to a remote target, for example, for biopsy or treatment, both the medical device and the target should be visible in some sort of a 3D guidance system.

A fluoroscopic imaging device is commonly located in the operating room during navigation procedures. The standard fluoroscopic imaging device may be used by a clinician, for example, to visualize and confirm the placement of a medical device after it has been navigated to a desired location. However, although standard fluoroscopic images display highly dense objects such as metal tools and bones as well as large soft-tissue objects such as the heart, the fluoroscopic images may have difficulty resolving small soft-tissue objects of interest such as lesions. Furthermore, the fluoroscope image is only a two-dimensional projection. Therefore, an X-ray volumetric reconstruction may enable identification of such soft tissue objects and navigation to the target.

Several solutions exist that provide 3D volume reconstruction such as CT and cone-beam CT which are extensively used in the medical world. These machines algorithmically combine multiple X-ray projections from known, calibrated X-ray source positions into 3D volume in which, inter alia, soft-tissues are more visible. For example, a CT machine can be used with iterative scans during procedure to provide guidance through the body until the tools reach the target. This is a tedious procedure, as it requires several full CT scans, a dedicated CT room and blind navigation between scans. In addition, each scan requires the staff to leave the room due to high-levels of ionizing radiation and exposes the patient to such radiation. Another option is a cone-beam CT machine, which is available in some operation rooms and is somewhat easier to operate but is expensive and like the CT only provides blind navigation between scans, requires multiple iterations for navigation and requires the staff to leave the room. In addition, a CT-based imaging system is extremely costly, and in many cases not available in the same location as the location where a procedure is carried out.

An imaging technology that uses standard fluoroscope devices to reconstruct local 3D volume in order to visualize and facilitate navigation to in-vivo targets, and to small soft-tissue objects in particular, is described in U.S. Patent Publication No. 2017/035379 to Weingarten et al., entitled SYSTEMS AND METHODS FOR LOCAL THREE DIMENSIONAL VOLUME RECONSTRUCTION USING A STANDARD FLUOROSCOPE, U.S. Patent Publication No. 2017/035380 to Barak et al., entitled SYSTEM AND METHOD FOR NAVIGATING TO TARGET AND PERFORMING PROCEDURE ON TARGET UTILIZING FLUOROSCOPIC-BASED LOCAL THREE DIMENSIONAL VOLUME RECONSTRUCTION, and U.S. Patent Publication No. 2018/0160991 to Weingarten et al., entitled SYSTEMS AND METHODS FOR LOCAL THREE DIMENSIONAL VOLUME RECONSTRUCTION USING A STANDARD FLUOROSCOPE, the entire contents of each of which are incorporated herein by reference.

In general, according to the systems and methods disclosed in the above-mentioned patent publications, a standard fluoroscope c-arm can be rotated, e.g., about 30 degrees, around a patient during a medical procedure, and a fluoroscopic 3D reconstruction (F3DR) of the region of interest is generated by a specialized software algorithm.

Such quick generation of a 3D reconstruction of a region of interest can provide real-time 3D imaging of the target area. Real-time imaging of the target and medical devices positioned in its area may benefit numerous interventional procedures, such as biopsy and ablation procedures in various organs, vascular interventions and orthopedic surgeries. For example, when navigational bronchoscopy is concerned, the aim may be to receive accurate information about the position of a biopsy catheter relative to a target lesion.

As another example, minimally invasive procedures, such as laparoscopy procedures, including robotic-assisted surgery, may employ intraoperative fluoroscopy to increase visualization, e.g., for guidance and lesion locating, and to prevent unnecessary injury and complications. Employing the above-mentioned systems and methods for real-time reconstruction of fluoroscopic 3D imaging of a target area and for navigation based on the reconstruction may benefit such procedures as well.

Still, it may not be an easy task to accurately identify and mark a target in the F3DR, in particular when the target is a small soft-tissue. Thus, there is a need for systems and methods for facilitating the identification and marking of a target in fluoroscopic image data, and in a F3DR in particular, to consequently facilitate the navigation to the target and the yield of pertinent medical procedures.

SUMMARY

The present disclosure is directed to systems, methods and computer program products for displaying an F3DR and for facilitating the identification and marking of a target by a user in the F3DR. Marking a target in an F3DR and especially in real-time may not be straight forward or a simple task, especially for the untrained user. Furthermore, it is desired to receive a selection of the target at two capture or view angles, while at least one of them would be different than AP (anteroposterior), as selection in AP position is usually easier. Marking of the target at two such angles enhances the accuracy of the target localization. Thus, marking of the target performed at two stages, specifically when the first stage includes marking in AP position, facilitates the user's identification of the target and provides a better accuracy in the localization of the target, better registration between imaging modalities, and therefrom better results in treatment.

There is provided in accordance with the present disclosure a system for facilitating identification and marking of a target in a displayed Fluoroscopic Three-Dimensional Reconstruction (F3DR) of a body region of a patient. The system includes a display and one or more storage devices having stored thereon instructions for receiving an initial selection of the target in the F3DR, fining the F3DR based on the initial selection of the target, displaying the fined F3DR on the display, and receiving a final selection of the target in the fined F3DR via a user. The system further includes at least one hardware processor configured to execute said instructions.

In an aspect, the one or more storage devices have stored thereon further instructions for receiving a selection of a medical device in two two-dimensional fluoroscopic images, wherein the medical device is located in an area of the target, and initially fining the F3DR based on the selection of the medical device prior to fining the F3DR based on the initial selection of the target. Such a selection of the medical device may be performed prior to the selection or marking of the target. Additionally, the one or more storage devices have stored thereon further instructions for displaying the initially fined F3DR on the display and wherein the initial selection of the target is received via a user selection. The two-dimensional fluoroscopic images may be displayed on the display and the selection of the medical device in the two-dimensional fluoroscopic images may be received via a user selection.

In an aspect, the one or more storage devices have stored thereon further instructions for receiving a CT scan of the body region of the patient, wherein the CT scan includes a marking of the target, generating at least one virtual fluoroscopy image based on the CT scan, wherein the virtual fluoroscopy image includes the target and the marking of the target, and displaying the virtual fluoroscopy image. Displaying the fined F3DR may include displaying different slices of the fined F3DR and may be according to commands provided by the user such as a user selection. Additionally, or alternatively, displaying the fined F3DR includes displaying the fined F3DR at different capture angles and may be according to commands provided by the user such as a user selection.

Receiving of the final selection of the target in the fined F3DR may include directing the user to identify and mark the target in two fluoroscopic slice images of the fined F3DR captured at two different angles. Additionally, or alternatively, receiving of the final selection of the target in the fined F3DR may include indicating proper ranges of capture angles in which the target should be marked. In an aspect, the target is a soft-tissue target.

In an aspect, the system further includes a fluoroscopic imaging device and the one or more storage devices have stored thereon further instructions for acquiring a sequence of fluoroscopic images of the body region about a plurality of angles relative to the body region while a medical device is positioned in a target area, generating the F3DR of the body region based on the sequence of fluoroscopic images, and determining an offset of the medical device with respect to the target based on the selection of the medical device and at least one of the initial selection of the target or the final selection of the target. The target area may include at least a portion of lungs and the medical device may be configured to be navigated to the target area through a luminal network of lungs.

In an aspect, the one or more storage devices have stored thereon further instructions for receiving a three-dimensional imaging of the body region of the patient, wherein the three-dimensional imaging includes a marking of the target, and displaying the three-dimensional imaging. The three-dimensional imaging may be a CT or an MRI scan.

In an aspect, the system is used during a medical procedure, and the three-dimensional imaging is a pre-operative imaging which was used in a planning phase of the medical procedure.

In another aspect of the present disclosure a method for facilitating identification and marking of a target in a displayed F3DR of a body region of a patient is provided. The method includes using at least one hardware processor for receiving an initial selection of the target in the F3DR, fining the F3DR based on the initial selection of the target, displaying the fined F3DR on a display, and receiving a final selection of the target in the fined F3DR via a user.

In an aspect, the method includes using said at least one hardware processor for receiving a selection of a medical device in two two-dimensional fluoroscopic images, where the medical device is located in an area of the target, and initially fining the F3DR based on the selection of the medical device. Additionally, or alternatively, the method further includes at least one hardware processor for displaying the initially fined F3DR on the display, wherein the initial selection of the target is received via a user selection. In an aspect, the method further includes using said at least one hardware processor for displaying the two-dimensional fluoroscopic images on the display, wherein the selection of the medical device in the two-dimensional fluoroscopic images is received via a user selection.

In an aspect, the method includes using the at least one hardware processor for receiving a CT scan of the body region of the patient, wherein the CT scan includes a marking of the target, generating at least one virtual fluoroscopy image based on the CT scan, wherein the virtual fluoroscopy image includes the target and the marking of the target, and displaying the virtual fluoroscopy image on the display. Displaying of the virtual fluoroscopy image may be performed upon a user's request. Displaying of the fined F3DR may include displaying different slices of the fined F3DR and may be according to commands provided by the user such as a user selection. Additionally, or alternatively, displaying of the fined F3DR includes displaying the fined F3DR at different capture angles and may be according to commands provided by the user such as a user selection.

In an aspect, receiving of the final selection of the target in the fined F3DR includes directing the user to identify and mark the target in two fluoroscopic slice images of the fined F3DR captured at two different angles. Additionally, or alternatively, receiving of the final selection of the target in the fined F3DR includes indicating proper ranges of capture angles in which the target should be marked.

In an aspect, the method further includes using the at least one hardware processor for acquiring a sequence of fluoroscopic images of the body region via a fluoroscopic imaging device and about a plurality of angles relative to the body region, generating the F3DR of the body region based on the sequence of fluoroscopic images, and determining an offset of a medical device with respect to the target based on the selections of the target and the medical device, thereby facilitating navigation to an area of the target within the patient's body region during a medical procedure using real-time two-dimensional fluoroscopic images. Additionally, or alternatively, the method includes using the at least one hardware processor for receiving a three-dimensional imaging of the body region of the patient, wherein the three-dimensional imaging includes a marking of the target, and displaying the three-dimensional imaging.

The method may be used during a medical procedure, and the three-dimensional imaging is a pre-operative imaging which was used in a planning phase of the medical procedure.

In yet another aspect of the present disclosure, a non-transitory computer-readable storage medium encoded with a program that, when executed by a processor, performs a method for facilitating identification and marking of a target in a F3DR of a body region of a patient is provided. The method includes receiving a selection of a medical device in two two-dimensional fluoroscopic images, where the medical device is located in an area of the target, initially fining the F3DR based on the selection of the medical device, displaying the initially fined F3DR on a display, receiving an initial selection of the target in the initially fined F3DR via a user selection, further fining the F3DR based on the initial selection of the target, displaying the further fined F3DR on the display, and receiving a final selection of the target in the further fined F3DR via a user selection, thereby facilitating an identification and marking of the target in the F3DR.

BRIEF DESCRIPTION OF THE DRAWINGS

Various aspects and embodiments of the present disclosure are described hereinbelow with references to the drawings, wherein.

DETAILED DESCRIPTION

Figure 1:
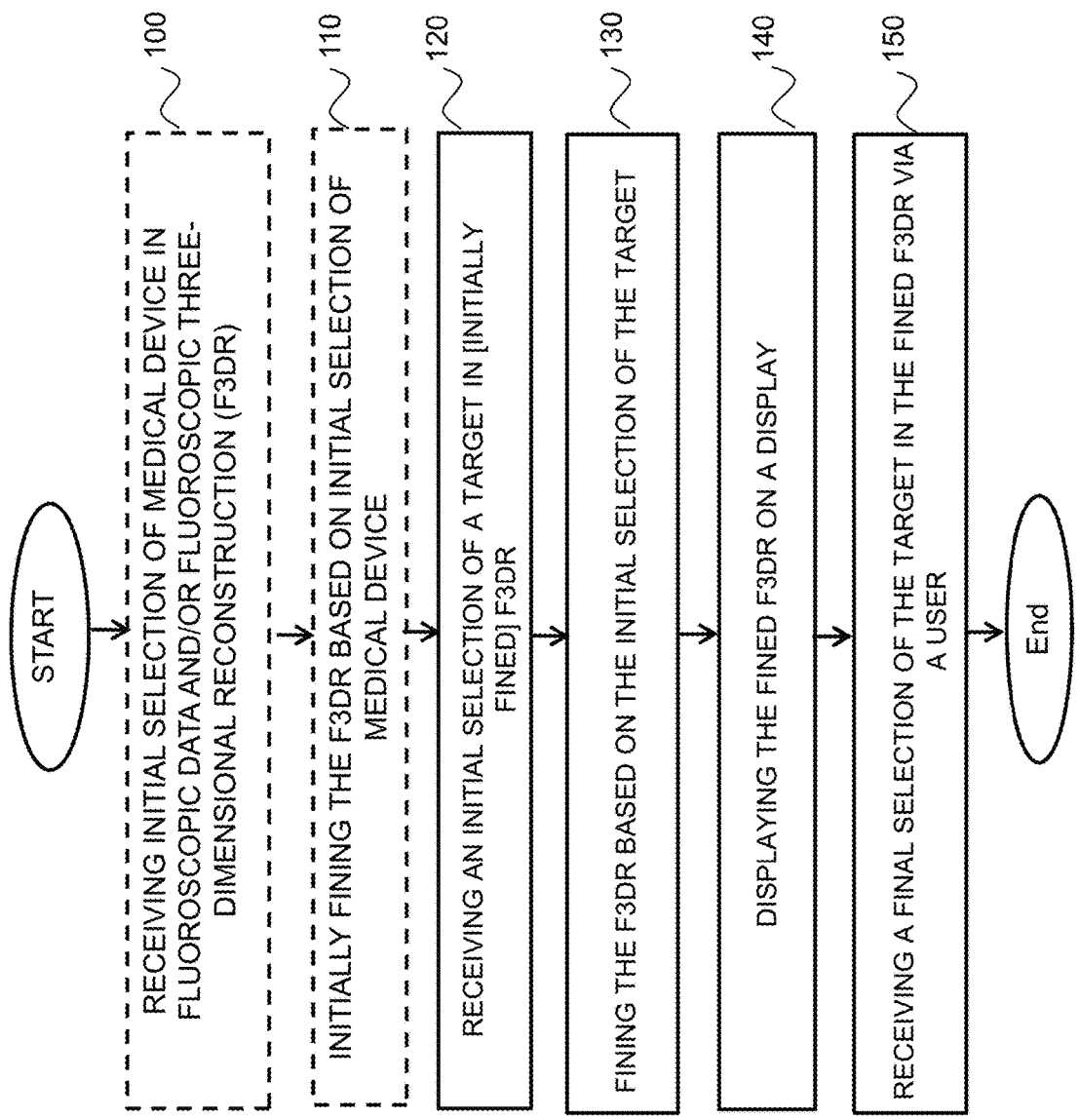
FIG. 1 is a flow chart of a method for displaying a F3DR and for identifying and marking a target in the F3DR in accordance with the present disclosure.

The term "target", as referred to herein, may relate to any element, biological or artificial, or to a region of interest in a patient's body, such as a tissue (including soft tissue and bone tissue), an organ, an implant or a fiducial marker.

The term "target area", as referred to herein, may relate to the target and at least a portion of its surrounding area. The term "target area" and the term "body region" may be used interchangeably when the term "body region" refers to the body region in which the target is located. Alternatively or in addition, the term "target area" may also refer to a portion of the body region in which the target is located, all according to the context.

The terms "and", "or" and "and/or" may be used interchangeably, while each term may incorporate the others, all according to the term's context.

The term "medical device", as referred to herein, may include, without limitation, optical systems, ultrasound probes, marker placement tools, biopsy tools, ablation tools (i.e., microwave ablation devices), laser probes, cryogenic probes, sensor probes, and aspirating needles.

The terms "fluoroscopic image", "fluoroscopic images", "fluoroscopy image", and "fluoroscopy images" may refer to a 2D fluoroscopic image/s and/or to a slice-image of a fluoroscopic 3D reconstruction, all in accordance with the term's context.

The terms "virtual fluoroscopic image", "virtual fluoroscopic images", "virtual fluoroscopy image", and "virtual fluoroscopy images" may refer to a virtual 2D fluoroscopic image/s and/or to a virtual fluoroscopy slice-image/s of a virtual fluoroscopic 3D reconstruction, or other 3D image data all in accordance with the term's context.

The present disclosure is directed to systems, methods and computer program products for displaying an F3DR and for facilitating the identification and marking of a target by a user in the F3DR. Marking a target in an F3DR and especially in real-time may not be straight forward or a simple task, especially for the untrained user. Furthermore, it is desired to receive a selection of the target at multiple capture or view angles (for example, two or three capture angles), while at least one of them would be different than AP (anteroposterior), as selection in AP position is usually easier. Marking of the target at two such angles enhances the accuracy of the target localization. Thus, marking of the target performed at two stages, specifically when the first stage includes marking in AP position, facilitates the user's identification of the target and provides a better accuracy in the localization of the target, better registration between imaging modalities, and therefrom better results in treatment.

In addition, using the initial target selection (e.g., at the first stage) to fine the F3DR further facilitates the final selection (e.g., at two different angles) and enhances its accuracy. Optionally, the process may be further enhanced by performing a two-stage fining of the F3DR by using a selection or marking of a medical device located in the target area to initially fine the F3DR.

Reference is now made to FIG. 1, which is a flow chart of a method for displaying a F3DR of a body region of a patient and for identifying and marking a target in the F3DR in accordance with the present disclosure. In some embodiments, that target may be a soft tissue target, such as a lesion and the body region may include at least a portion of the lungs. The method may begin either at step 100 or at step 120. To this end, steps 100 and 110 are optional steps. In step 100, a selection of a medical device in one or more fluoroscopy images or in a F3DR is received. Such a selection may be made from a single capture angle or from multiple capture angles. Additionally, the selection of the medical device in step 100 may be automatically made by the system via a dedicated algorithm or may be made by a user's selection. In an aspect, the selection of the medical device is performed in 2D fluoroscopic images, in particular, in at least two images. In an aspect, the medical device is marked or selected before the generation of the F3DR and the marking may be used for the generation/reconstruction of the F3DR.

In step 110, the F3DR is initially fined based on the received selection of the medical device in step 100. The initial fining of the F3DR in step 100 may include determining a range for the slice scrolling. In this aspect, the range is determined such that only a portion of the F3DR, which includes the selection of the medical device, is displayed and may be scrolled through. Thus, in this aspect, less slices are displayed to the user. One benefit of fining in this manner is that less slices are processed (e.g., fined), thereby reducing the use of computing resources and speeding the fining process. Additionally, or alternatively, the F3DR may be initially fined by decreasing the thickness of the slices thus achieving a better resolution for display. One benefit of fining in this manner is that a user may be presented with sharpened slices, thereby offering a better visualization of the target area and objects (e.g., medical devices, targets, etc.) located therein.

In an aspect, the thickness of the slices is predetermined. Although thinning the slices provides a better resolution, there may be a toll on thinning. That is, when slices are thinned, the volume appears more smeared and thus it becomes more difficult for the user to identify the target. Therefore, at the initial fining (step 110), a predetermined thickness is used which provides optimal results, taking into consideration the above. At the second stage, as described below (in step 130), the scroll range is decreased, the thickness of the slices is decreased, again to a predetermined thickness, or both the scroll range is decreased and the thickness of the slices is decreased.

In step 120, an initial selection of the target in the F3DR is received. As described above, in aspects, this method begins at step 120 and the initial selection of the target is made in the F3DR. Alternatively, where the method begins at step 100, the initial selection of the target in step 120 is made in the initially fined F3DR (as initially fined in step 110). The initial selection of the target may be automatic via a dedicated algorithm or may be performed by a user's selection, e.g., by identifying and marking the target in the displayed F3DR.

Figure 3A:
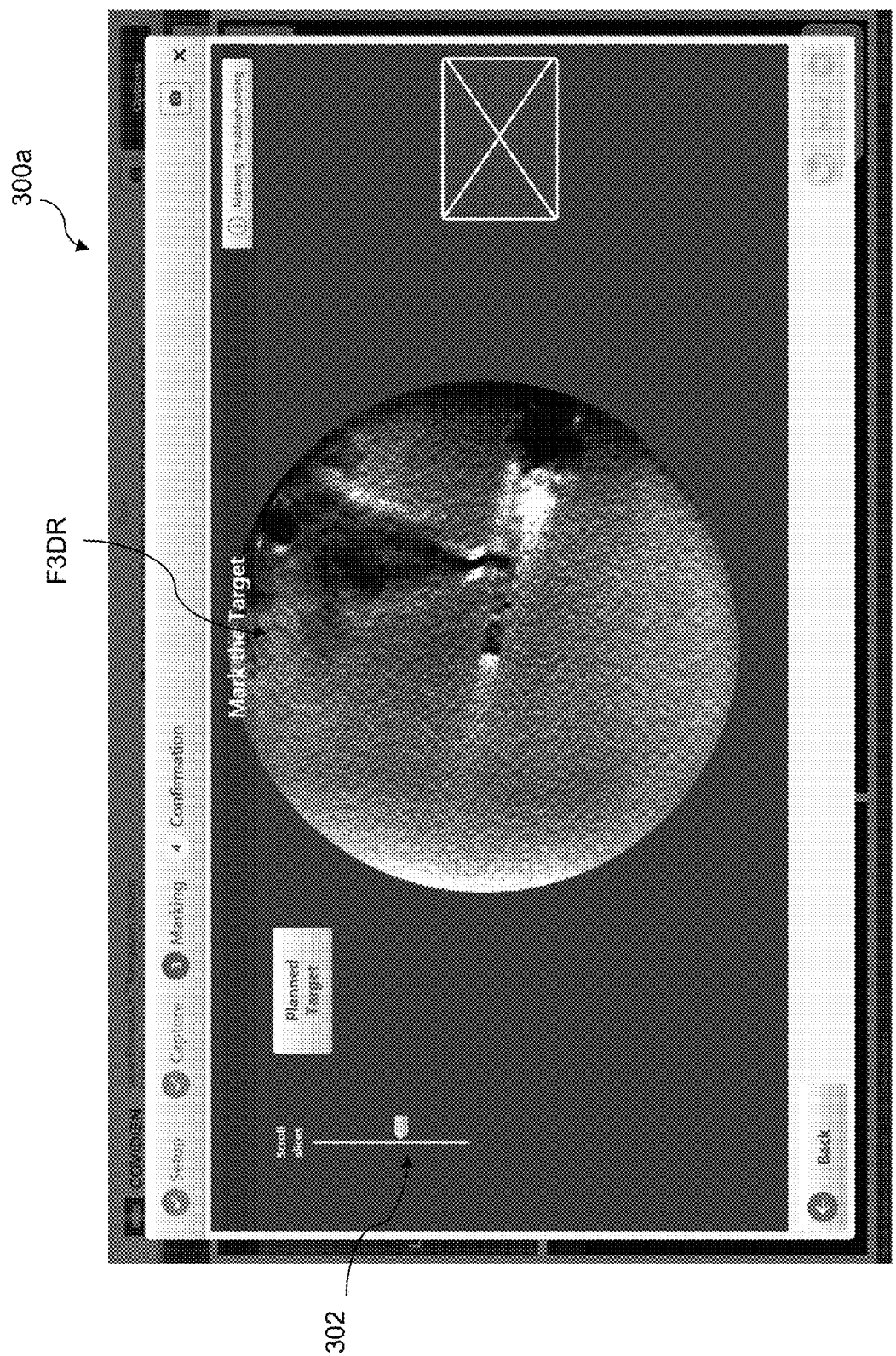
FIG. 3A is an exemplary screen shot showing a display of a F3DR in accordance with the present disclosure.
Figure 3B:
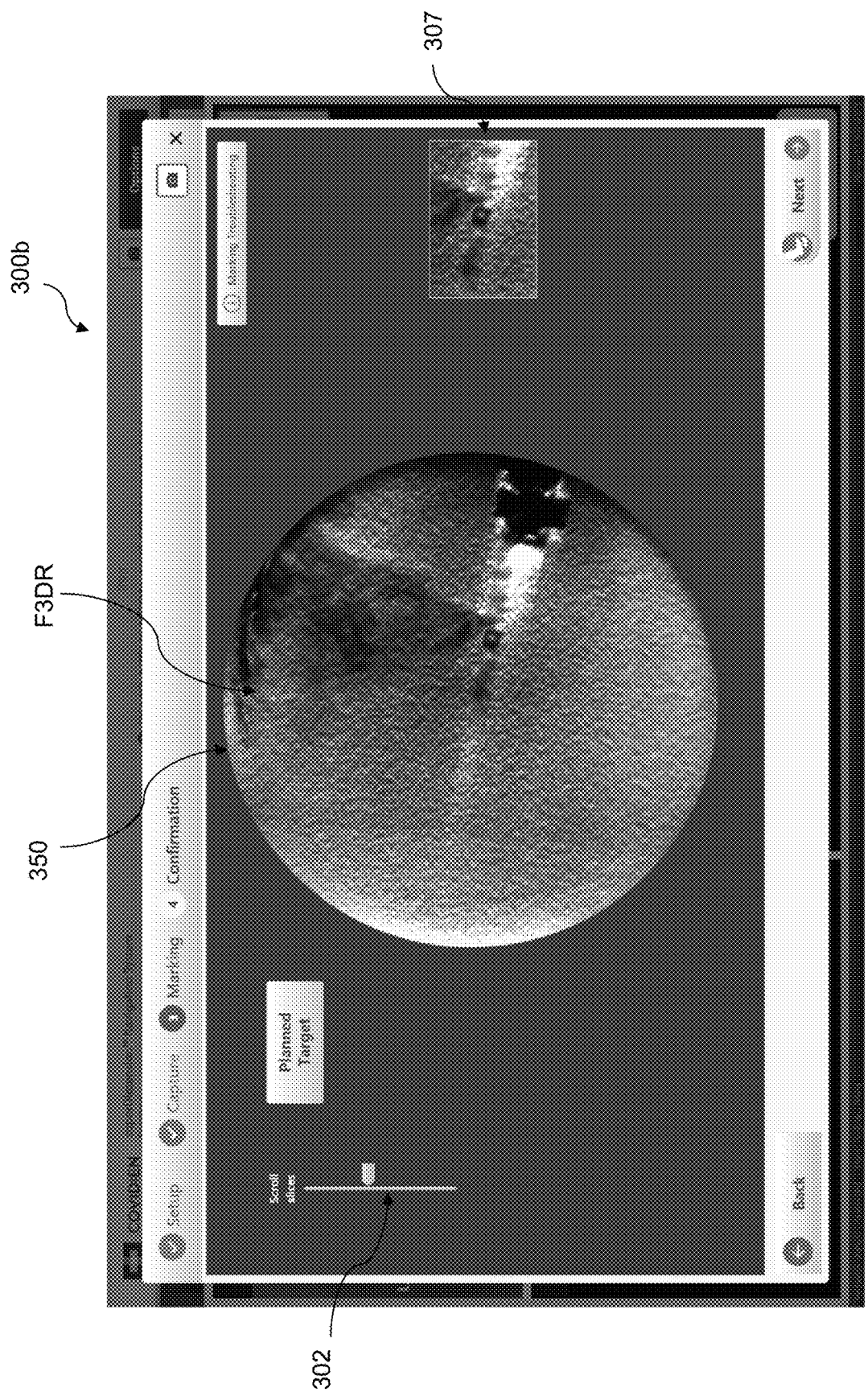
FIG. 3B is an exemplary screen shot showing an initial selection of a target in the F3DR of FIG. 3A.

Reference is now briefly made to FIGS. 3A-3B, which are screen shots of a user interface, which facilitates the selection of a target in an F3DR. FIG. 3A is an exemplary screen shot 300a showing a display of the F3DR and a scrolling bar 302 in accordance with the present disclosure. FIG. 3B is an exemplary screen shot 300b, showing an initial selection of the target "T" in the F3DR of FIG. 3A. The F3DR in this example is shown in AP position (anteroposterior) and includes slice images 305 through which the user may scroll by using a scroll bar 302. The thickness of the slice images 305 may be predetermined (e.g., number of pixels). In an aspect, the slice images 305 are slices of the F3DR. The user may then identify the target T in one of the slice images 305 and mark it, for example, by using a circular marking. For further convenience, an additional image 307 of the marked target T may be displayed, e.g., in a window adjacent to the F3DR. The additional image 307 may be any image including but not limited to a zoom-in image, a cropped image, a stretched image, or any combinations thereof. The aim is to mark the target T in the slice image 305 that displays it best or in a good enough visibility. To assist in this respect, the method includes the step of fining the image as described in further detail below.

In step 130, the F3DR (or the initially fined F3DR as initially fined in step 110) is fined based on the initial selection of the target. The F3DR may be fined by determining a range for the slice scrolling. The range is determined such that only a portion of the F3DR, which includes the marked target, is displayed and may be scrolled through. Thus, in this aspect, less slices are displayed to the user. One benefit of fining in this manner is that less slices are processed (e.g., fined), thereby reducing the use of computing resources and speeding the fining process. Additionally, or alternatively, the F3DR may be fined by decreasing the thickness of the slices thus achieving a better resolution for display. One benefit of fining in this manner is that a user may be presented with sharpened slices, thereby offering a better visualization of the target area and objects (e.g., medical devices, targets, etc.) located therein. As described above, at the second stage (in step 130), the scroll range is decreased, the thickness of the slices is decreased, again to a predetermined thickness, or both the scroll range is decreased and the thickness of the slices is decreased.

In step 140, the fined F3DR is displayed on a display. In some embodiments, the display of the fined F3DR may include displaying different slices of the fined F3DR and may be displayed according to commands provided by the user, e.g., through a slices scroll bar as shown in FIGS. 3A and 3B. In some embodiments, the display of the fined F3DR may include displaying the fined F3DR at different capture angles and according to commands provided by the user.

Figure 3C:
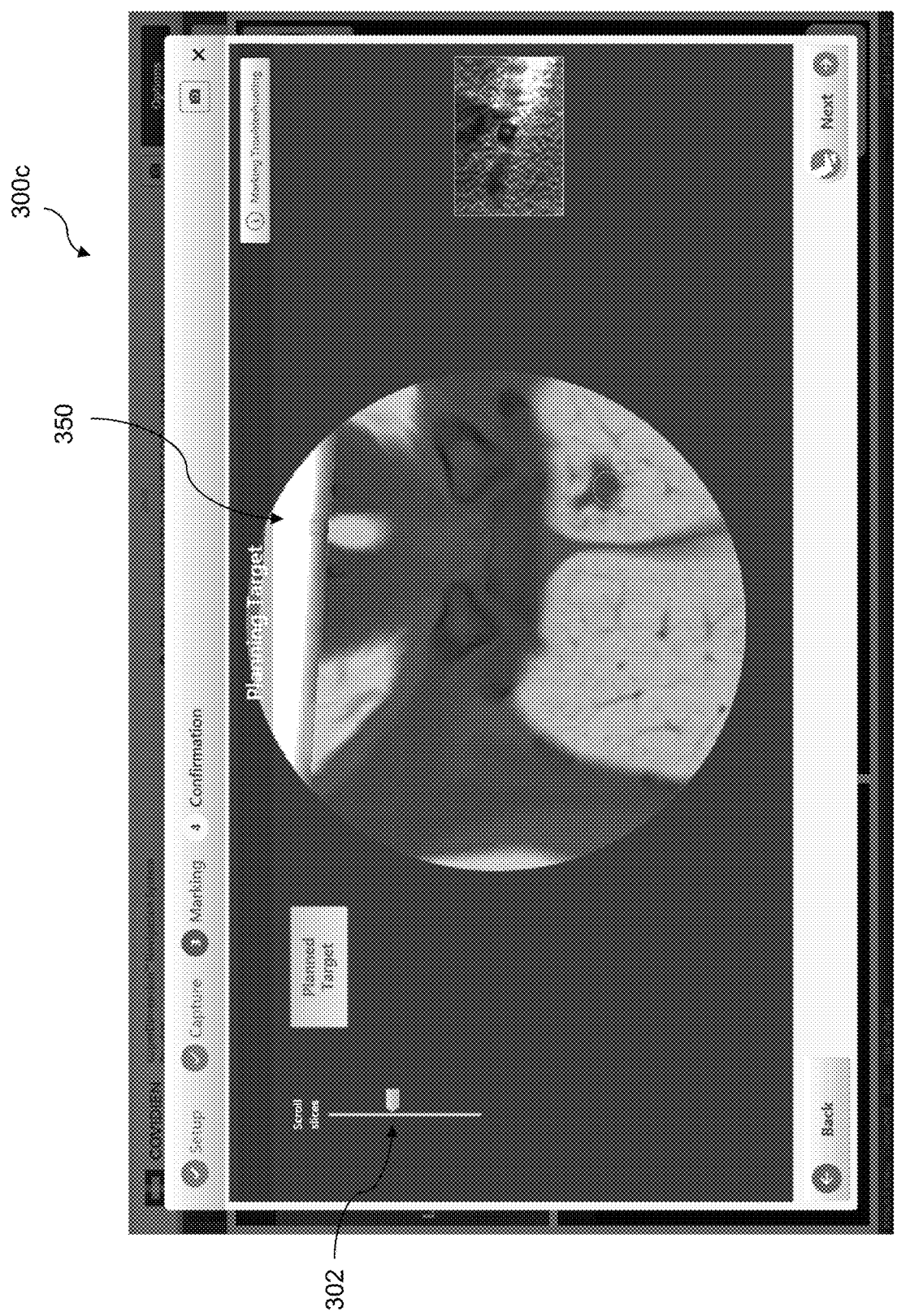
FIG. 3C is an exemplary screen shot showing a display of a virtual fluoroscopy image showing a previous selection of a target (for example, a previous selection of the target performed in a planning phase) in accordance with the present disclosure.
Figure 3D:
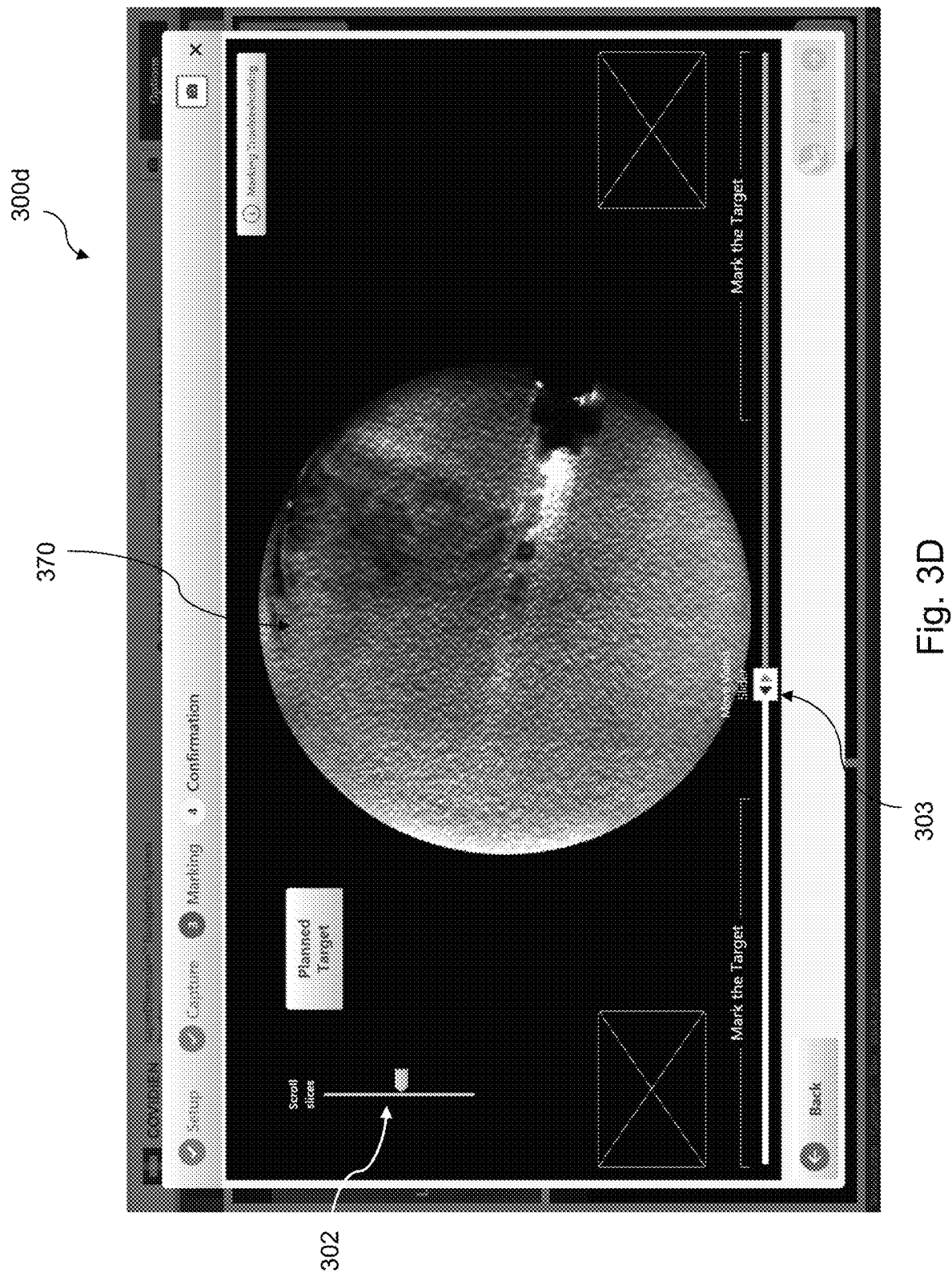
FIG. 3D is an exemplary screen shot showing a display of a fined F3DR in accordance with the present disclosure.

Reference is now made to FIG. 3D, which is an exemplary screen shot 300d showing a display of a fined F3DR 370 in accordance with the present disclosure. The display of the screen shot 300d includes the fined F3DR 370, the slices scroll bar 302 and a capture angle scroll bar 303, which allows the user to control the angle at which the fined F3DR 370 is displayed. By "capture angle" it is meant the angle at which the F3DR or fined F3DR 370 is captured or viewed.

In step 150, a final selection of the target T in the fined F3DR is received via a user. In some embodiments, the receiving of the final selection of the target may include directing the user to identify and mark the target or select the target in a single fluoroscopic (or F3DR) slice image. In some embodiments, the receiving of the final selection of the target may include directing the user to identify and mark the target or select the target in two fluoroscopic slice images of the fined F3DR captured at two different angles. Identifying and marking the target or selecting the target in two or more slice images captured at different angles, as opposed to one, may enhance the localization of the target to achieve a better accuracy, e.g., by using triangulation. Thus, the target may be located within the slice image (which has a certain thickness). In some embodiments, the receiving of the final selection of the target in the fined F3DR in step 150 may further include indicating the proper ranges of capture angles in which the target should be marked. In some embodiments, the selection of the slices may be limited to such proper ranges of capture angles. The proper ranges of the two capture angles may be determined to provide enough distance between the two angles to achieve a good enough accuracy in the target localization within the F3DR.

Displaying the fined F3DR, e.g., a portion of the F3DR surrounding the initially identified target, in step 140 may facilitate the selection of the target (for example in step 150). Specifically, it may facilitate the selection of the target in two slices captured at different angles. Selection of the target in two such slices may be more time consuming and may be more difficult than, for example, selecting the target when the F3DR is positioned in AP.

Figure 3E:
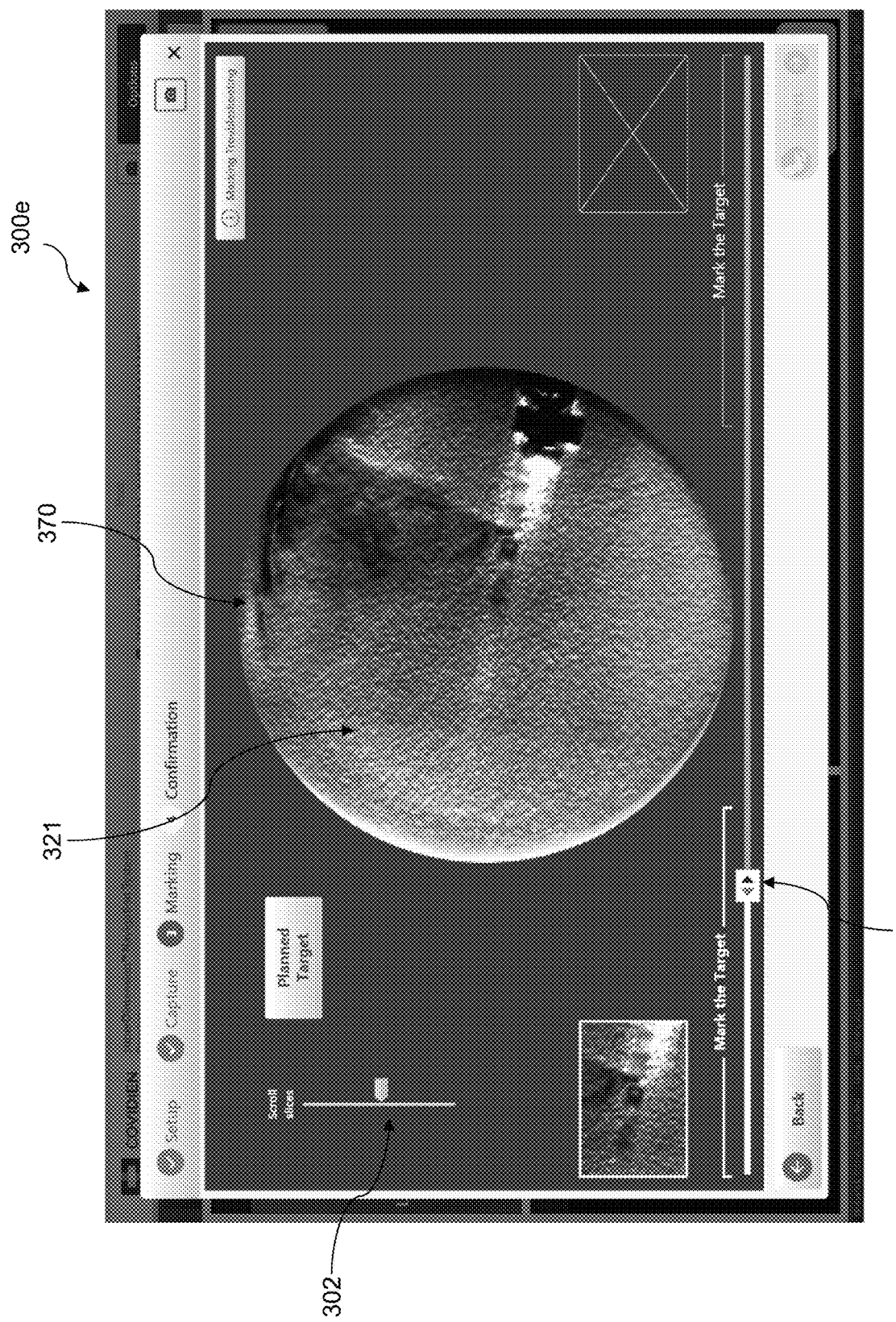
FIG. 3E is an exemplary screen shot of a final selection of the target in a slice image of the fined F3DR while captured at a first capture angle in accordance with the present disclosure.
Figure 3F:
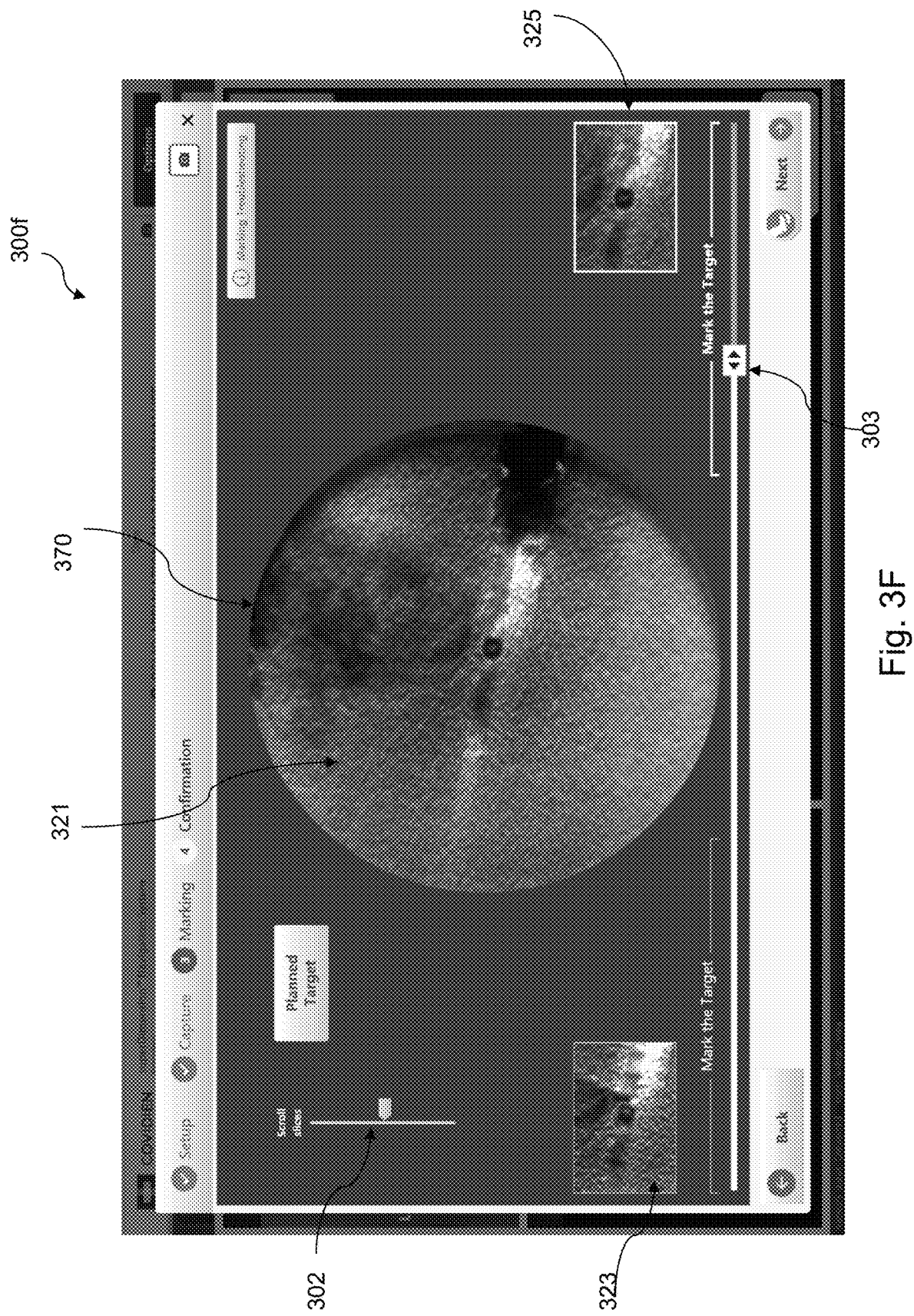
FIG. 3F is an exemplary screen shot of a final selection of the target in a slice image of the fined F3DR while captured at a first capture angle and a second capture angle in accordance with the present disclosure.

Reference is now made to FIGS. 3E and 3F. FIG. 3E is an exemplary screen shot 300e of a final selection of the target T in a slice image 321 of the fined F3DR while captured at a first capture angle in accordance with the present disclosure. FIG. 3F is an exemplary screen shot 300f of a final selection of the target T in a slice image 321 of the fined F3DR 370 while captured at a first capture angle and a second capture angle in accordance with the present disclosure. According to the exemplary user interface shown in FIGS. 3E and 3F, the user may mark a target T, which is shown only in slices 321 in the delimited areas of the capture angles scroll bar 303. When the user marks a target T, a close-up image of the marked target is displayed in a window for each of the first capture angle and the second capture angle. As shown in the exemplary screen shot 300f of FIG. 3F, a first window 323 is displayed with the target T at the first capture angle and a second window 325 is displayed with the target T at the second capture angle.

As described above with reference to steps 100 and 110, in some embodiments, a selection of a medical device in two two-dimensional (2D) fluoroscopic images may be received, where the medical device is located in the area of the target. The F3DR may be then initially fined based on the selection of the medical device. The 2D fluoroscopic images may be related to the F3DR via their capture angles. The initial selection of the target may be then performed in the initially fined F3DR, thus facilitating the initial selection of the target. In some embodiments, the two-dimensional fluoroscopic images may be displayed on the display and the selection of the medical device may be received via automatic detection algorithms or via the user's selection. In some embodiments, the initially fined F3DR may be displayed on the display and the initial selection of the target may be received via the user's selection.

Figure 4A:
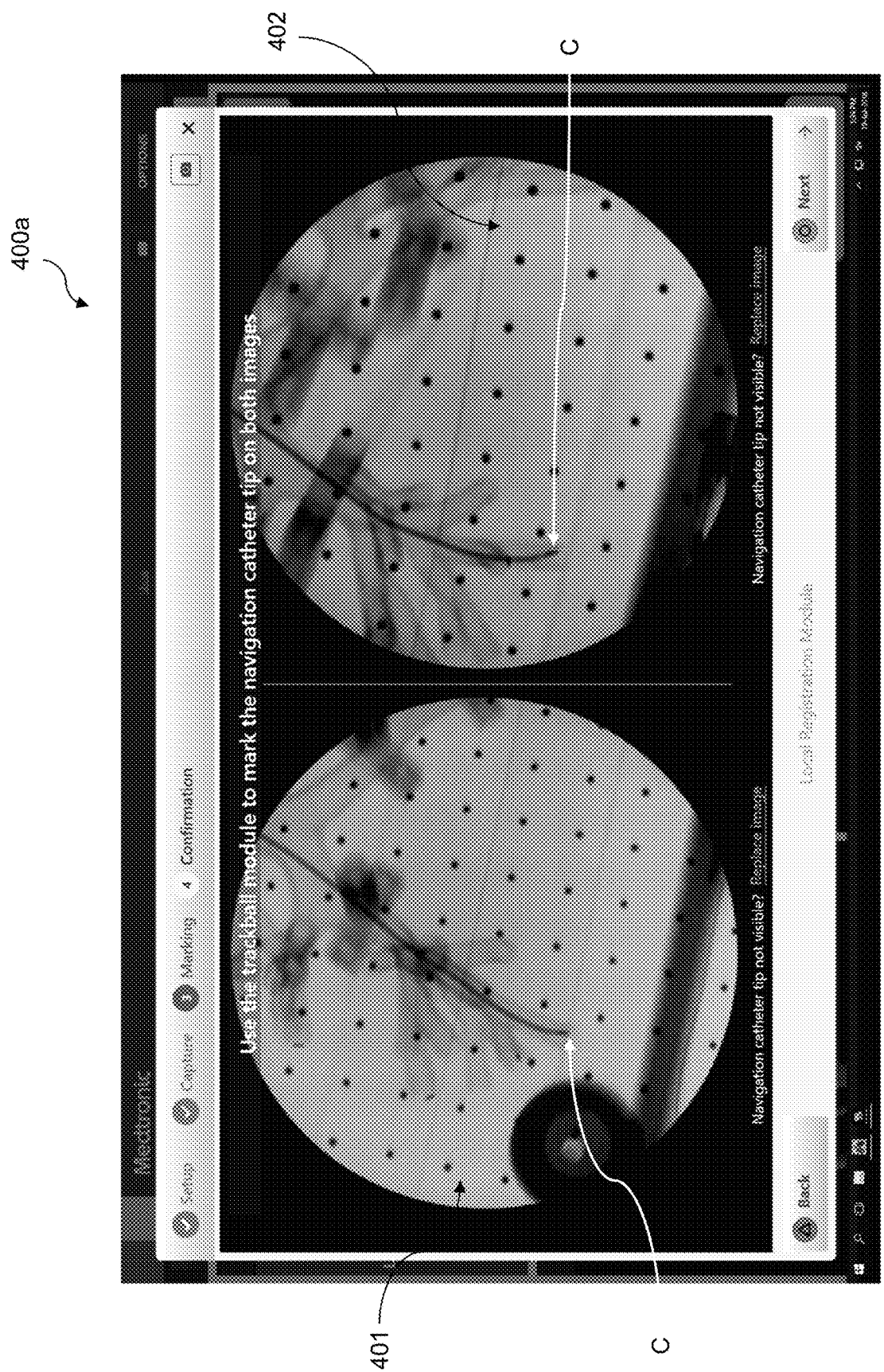
FIG. 4A is an exemplary screen shot showing a selection of a medical device in two two-dimensional fluoroscopic images in accordance with the present disclosure.
Figure 4B:
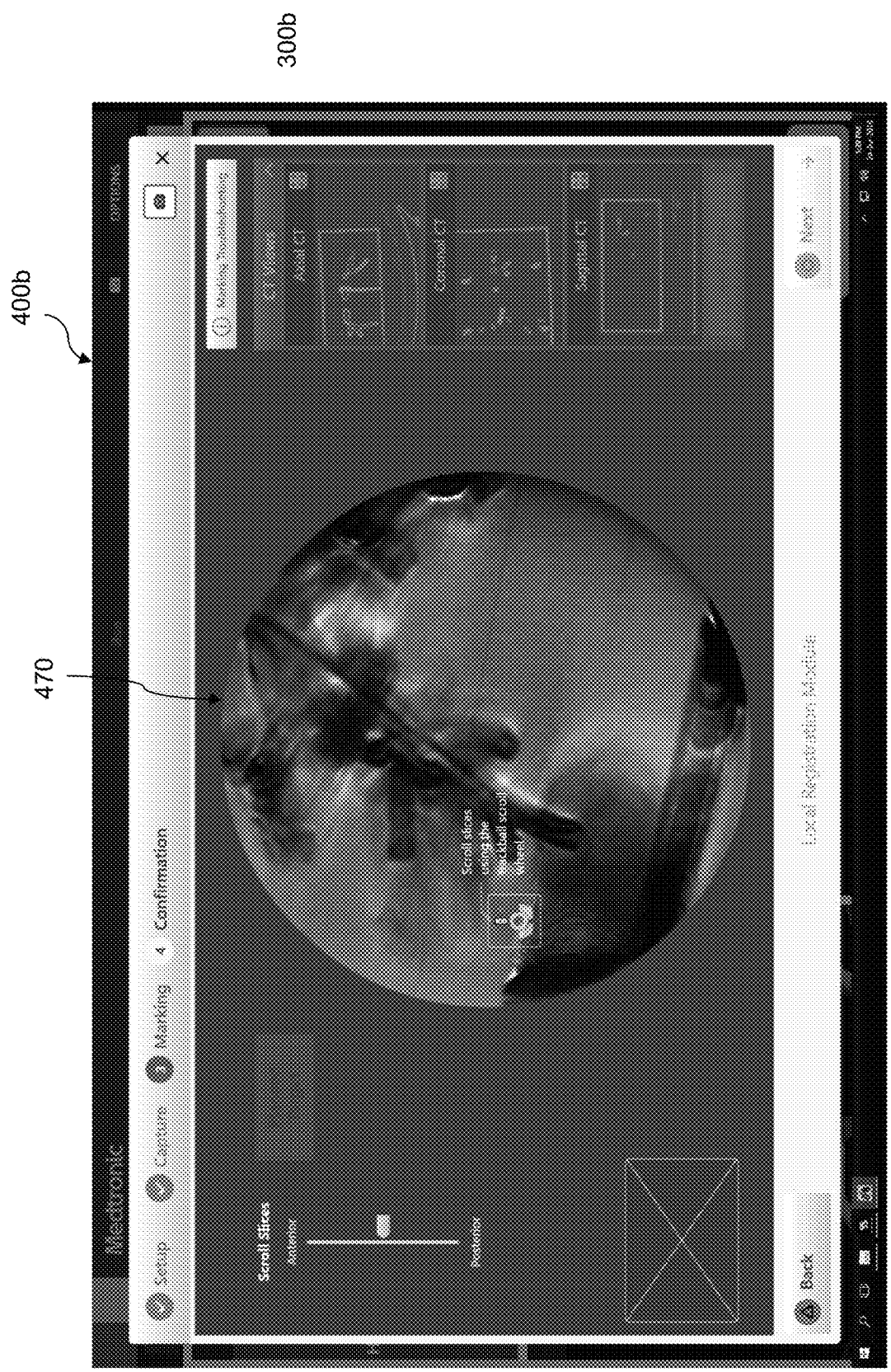
FIG. 4B is an exemplary screen shot showing a first selection of a target in an initially fined F3DR in accordance with the present disclosure.

Reference is now made to FIGS. 4A-4F, which are screen shots of another user interface that facilitates the selection of a target in an F3DR. FIG. 4A is an exemplary screen shot 400a showing a selection of a catheter "C" in two two-dimensional fluoroscopic images, namely first two-dimensional fluoroscopic image 401 and second two-dimensional fluoroscopic image 402, in accordance with the present disclosure. FIG. 4B is an exemplary screen shot 400b showing a first selection of a target T in an initially fined F3DR 470, in accordance with the present disclosure.

In some embodiments, a CT scan of the body region of the patient, which includes a marking of the target, may be received. At least one virtual fluoroscopy image, for example, virtual fluoroscopy image 350 (FIG. 3C) or virtual fluoroscopy image 450 (FIG. 4D), which includes the target and the marking of the target may be generated based on the CT scan. The virtual fluoroscopy image may be then displayed on the display and may be used by the user as a reference when selecting the target in the F3DR (e.g., when performing an initial and/or final selection of the target). In some embodiments, the virtual fluoroscopy image may be displayed upon the user's request. In some embodiments, the virtual fluoroscopy image and the F3DR may be displayed simultaneously. In other embodiments, the virtual fluoroscopy image and the F3DR may be displayed alternatively. Further details with respect to the display, generation and use of the virtual fluoroscopy image are described in U.S. patent application Ser. No. 16/022,222 to Weingarten et al., entitled SYSTEM AND METHOD FOR IDENTIFYING, MARKING AND NAVIGATING TO A TARGET USING REAL TIME TWO DIMENSIONAL FLUOROSCOPIC DATA, the entire contents of which are incorporated herein by reference.

Reference is now made to FIG. 3C, which is an exemplary screen shot 300c showing a display of a virtual fluoroscopy image 350 in accordance with the present disclosure. According to the example shown in FIG. 3A-3F, the virtual fluoroscopy image 350 is displayed upon the user's request or command, e.g., by pressing a "Planned Target" button, and may be displayed at any stage of the target selection. In this example, the virtual fluoroscopy image 350 is displayed instead of the F3DR, but it is appreciated that the virtual fluoroscopy image 350 may be displayed along with (e.g., adjacent) the displayed F3DR.

In some embodiments, the method may further include acquiring the sequence of fluoroscopic images of the body region via a fluoroscopic imaging device and about a plurality of angles relative to the body region. The F3DR may be then generated based on the sequence of fluoroscopic images. An offset of the medical device with respect to the target may be determined based on the selections of the target and the medical device. Such offset determination based on two-dimensional fluoroscopic images captured in real-time may be used to facilitate navigation to an area of the target during a medical procedure. The real-time target-medical-device offset may be used, for example and without limitation, to correct navigation (e.g., displayed or calculated positions of a catheter) and generate local F3DR-CT scan registration. In some embodiments, the target area may include at least a portion of the lungs and the medical device is configured to be navigated to the target area through the airway's luminal network. Generation of such an F3DR and the uses of the above offset are described in U.S. Patent Publication No. 2017/035379 to Weingarten et al., entitled SYSTEMS AND METHODS FOR LOCAL THREE DIMENSIONAL VOLUME RECONSTRUCTION USING A STANDARD FLUOROSCOPE, U.S. Patent Publication No. 2017/035380 to Barak et al., entitled SYSTEM AND METHOD FOR NAVIGATING TO TARGET AND PERFORMING PROCEDURE ON TARGET UTILIZING FLUOROSCOPIC-BASED LOCAL THREE DIMENSIONAL VOLUME RECONSTRUCTION, and provisional U.S. Patent Application No. 62/628,017 to Barak et al., entitled SYSTEM AND METHOD FOR POSE ESTIMATION OF AN IMAGING DEVICE AND FOR DETERMINING THE LOCATION OF A MEDICAL DEVICE WITH RESPECT TO A TARGET, the entire contents of each of which are incorporated herein by reference.

In some embodiments, the method may further include receiving three-dimensional (3D) imaging of the body region of the patient, which includes a marking of the target. The 3D imaging may be, for example, a CT scan or an MRI scan data set. The 3D imaging may be then displayed. The 3D imaging may be used by the user as a reference when performing an initial and/or final selection of the target. Utilizing a 3D view of the target for identifying the target in another 3D view, e.g., the F3DR, may be advantageous. The 3D imaging may be displayed upon the user's request or command. The 3D imaging and the F3DR and/or a virtual fluoroscopy image may be displayed simultaneously and/or alternatively. In some embodiments, when the disclosed methods are used during a medical procedure (e.g., identifying a target via real-time fluoroscopic 3D images), a pre-operative 3D imaging data set, which was used in a planning phase of the procedure may be used. Using images, e.g., which were used for identifying the target and planning the navigation to the target, may be very advantageous in performing identification and marking (e.g., selection) of the target in a real-time three-dimensional volume, reconstruction or rendering.

Figure 4C:
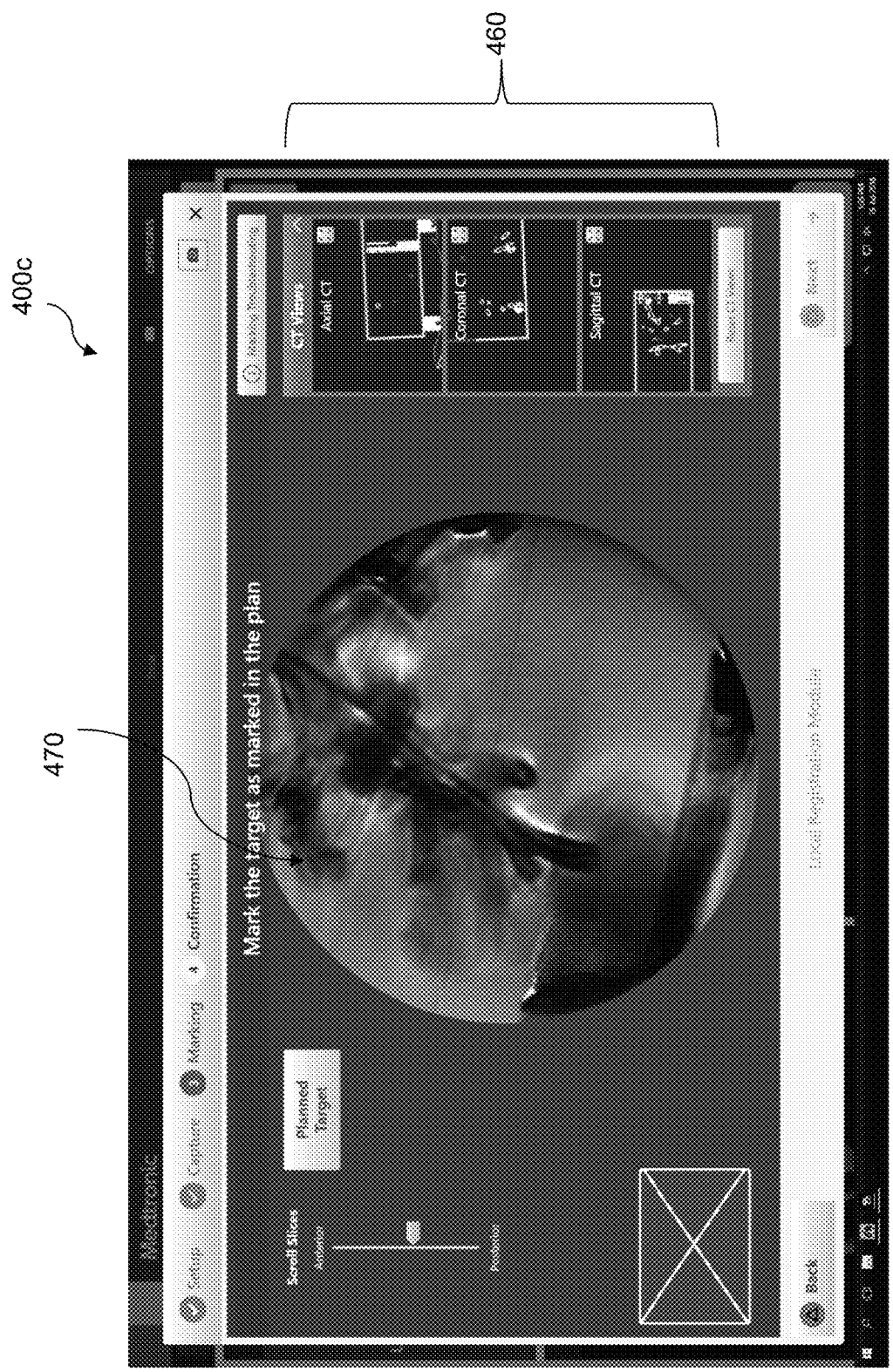
FIG. 4C is an exemplary screen shot showing a display of the initially fined F3DR and of slice images of a CT scan in accordance with the present disclosure.
Figure 4D:
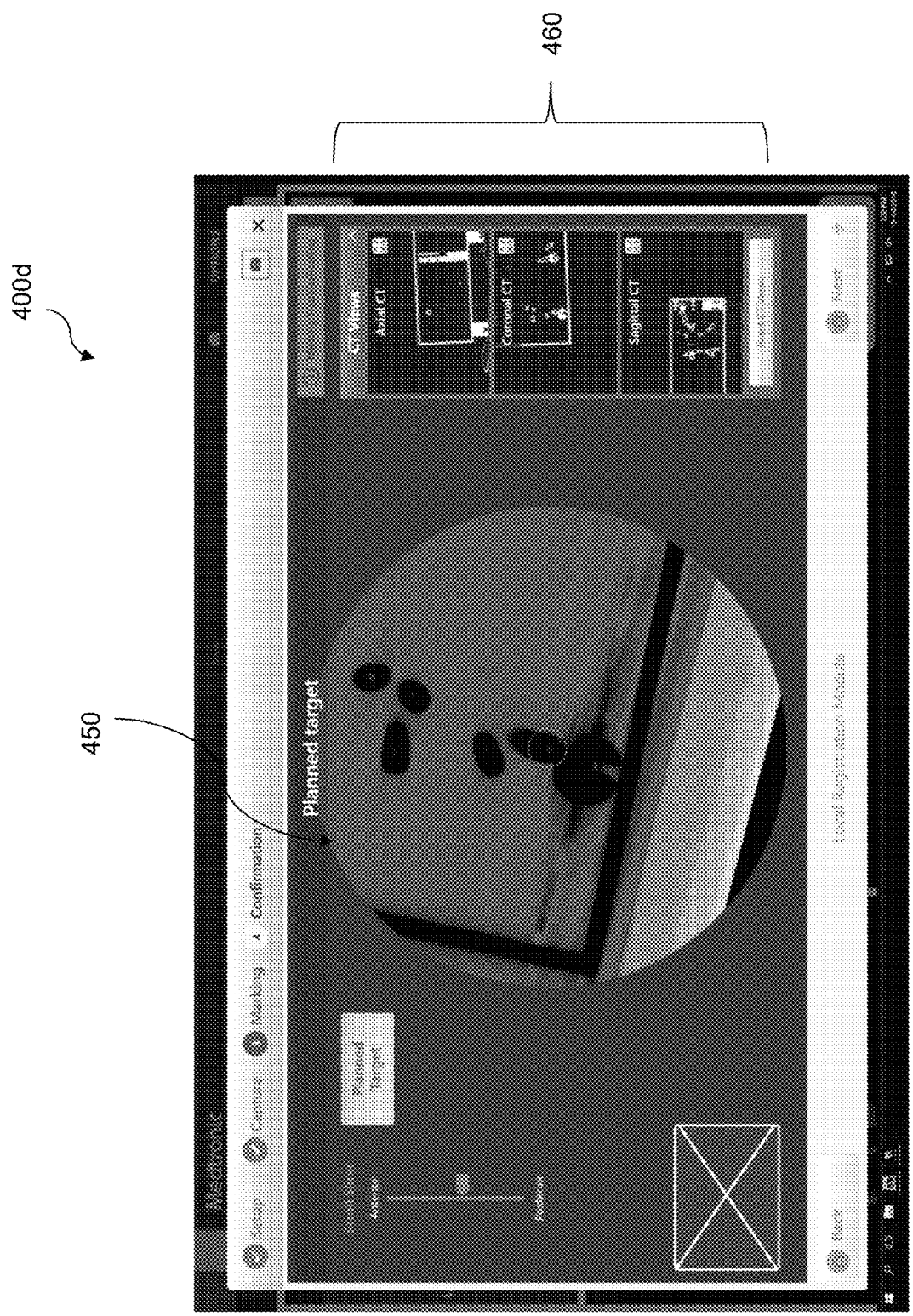
FIG. 4D is an exemplary screen shot showing a display of a virtual fluoroscopy image and of the slice images of a CT scan in accordance with the present disclosure.
Figure 4E:
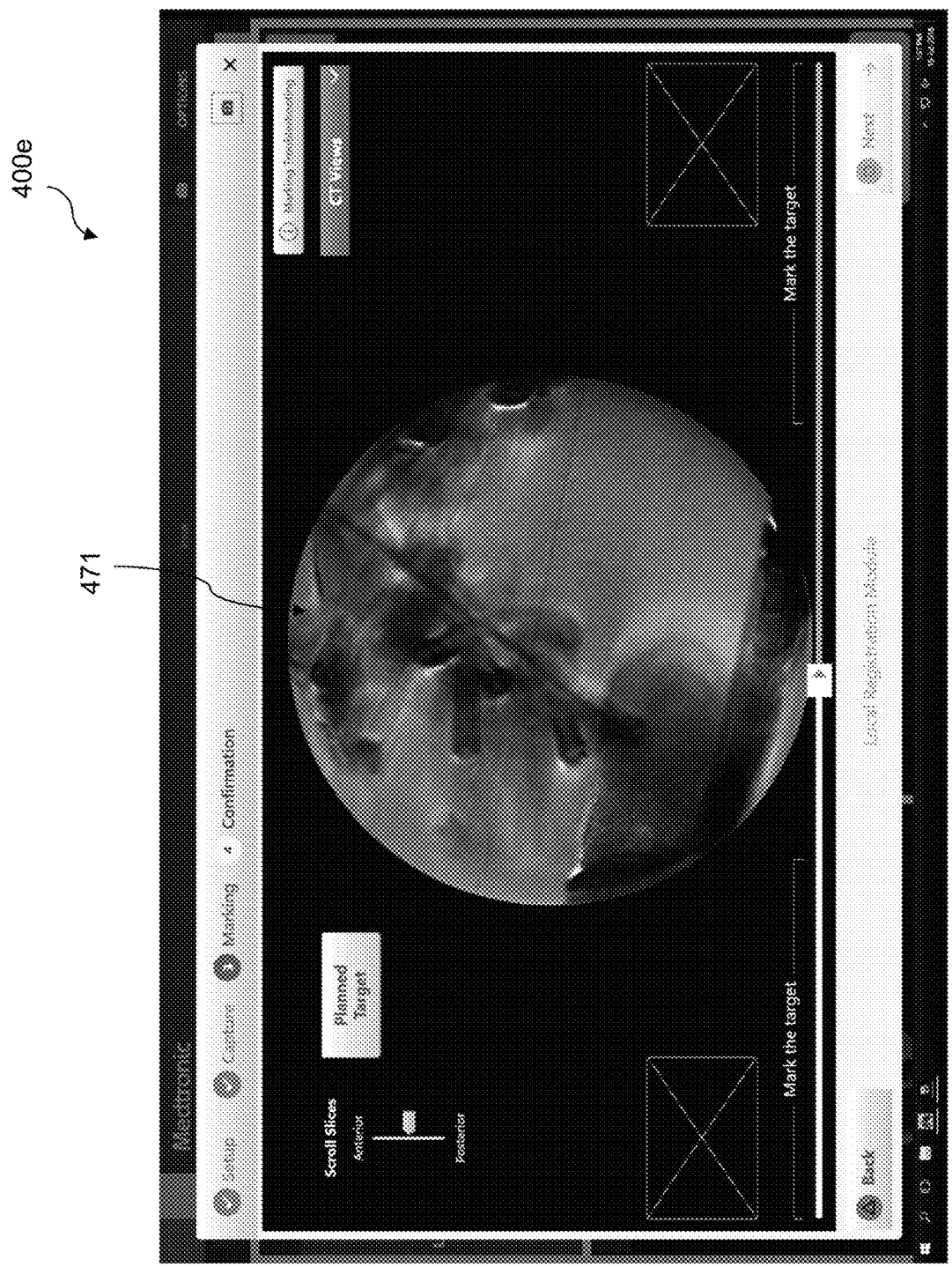
FIG. 4E is an exemplary screen shot showing a display of the fined F3DR in accordance with the present disclosure.

Reference is now made to FIGS. 4C-4E. FIG. 4C is an exemplary screen shot 400c showing a display of the initially fined F3DR 470 and of slice images 460 of a CT scan in accordance with the present disclosure. In this specific example, the slice images 460 of the CT scan may be displayed upon the user's command. The CT scan is displayed by displaying three views of the CT (e.g., axial, coronal and sagittal) which may provide the user with the option to create a 3D mental image of the target area that can help in identifying the target in the real-time F3DR. The default slices displayed in FIG. 4C are the slices at which the user marked the target at the planning phase of a medical procedure. The user may scroll or page through the slices. Additionally, the user may select an enlarge button to enlarge any of the slice images 460 for a more detailed view of the displayed slice. In some embodiments, other views of the CT used in the planning phase may be displayed.

FIG. 4D is an exemplary screen shot 400d showing a display of a virtual fluoroscopy image 450 and of the slice images 460 of a CT scan in accordance with the present disclosure. In this example, the virtual fluoroscopy image 450 is displayed instead of the F3DR and is displayed adjacent to the slice images 460 of the CT scan. FIG. 4E is an exemplary screen shot 400e showing a display of the fined F3DR 471 in accordance with the present disclosure.

Figure 4F:
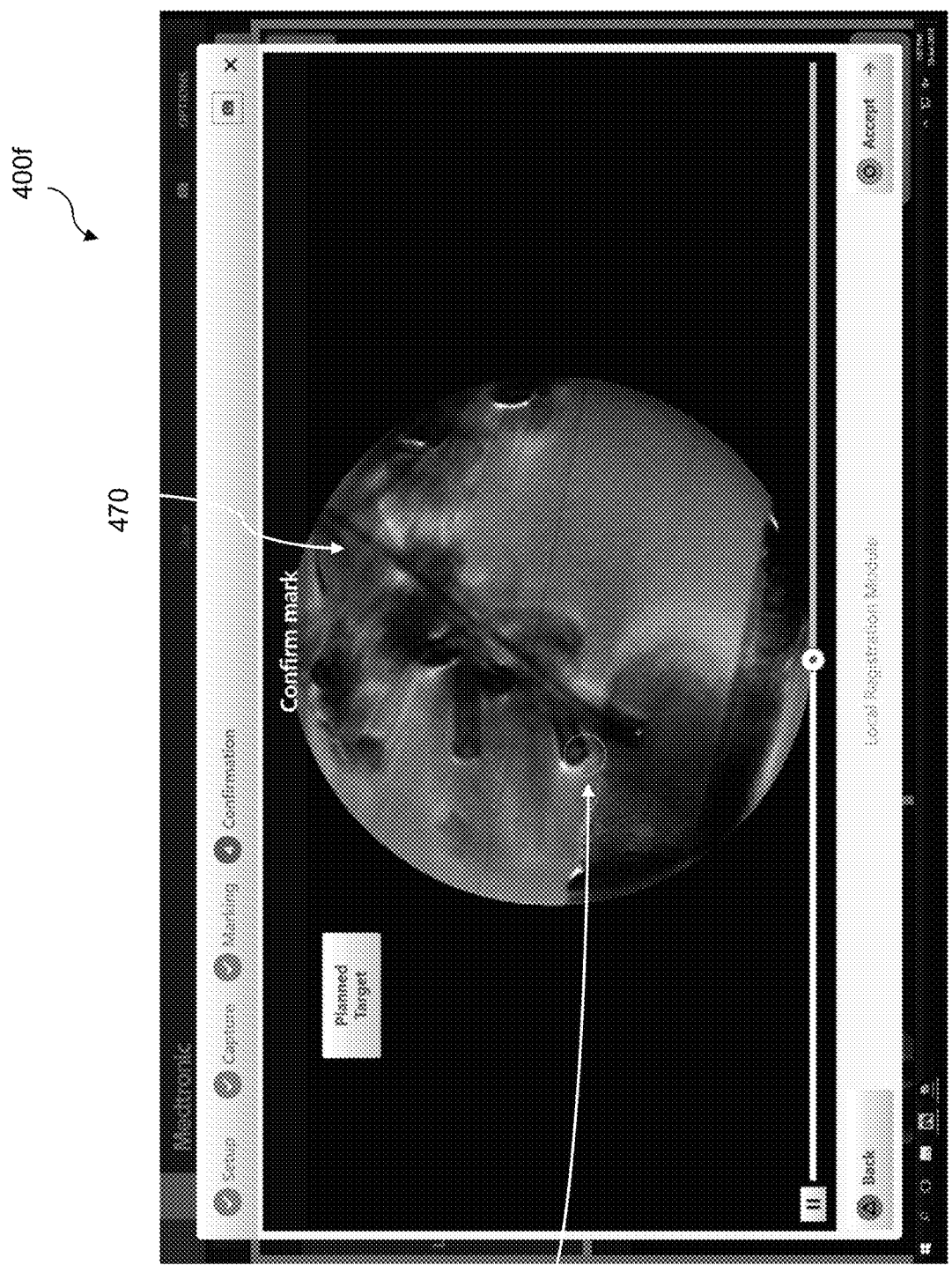
FIG. 4F is an exemplary screen shot showing a clip of the F3DR for confirming the selection of the target in accordance with the present disclosure.

In some embodiments, after the final selection of the target is performed, the target as selected may be displayed to the user and the user may be requested to confirm the selection. Reference is now made to FIG. 4F, which is an exemplary screen shot 400f showing a clip 470 of the F3DR for confirming the selection of the target T in accordance with the present disclosure. The F3DR including the marking of the target T (e.g., a circular marking) and optionally a marking of the catheter (e.g., a plus or cross-hair marking) may be displayed. In order to further confirm the selection, a clip 470 may be displayed which shows the F3DR with the markings at the different capture angles (e.g., the angles at which the 2D fluoroscopic images used to generate the F3DR were captured).

A computer program product for displaying a F3DR and for identifying, marking and navigating to a target is herein disclosed. The computer program product may include a non-transitory computer-readable storage medium having program code embodied therewith. The program code may be executable by at least one hardware processor to perform the steps of the method of FIG. 1 and as disclosed herein above.

Figure 2:
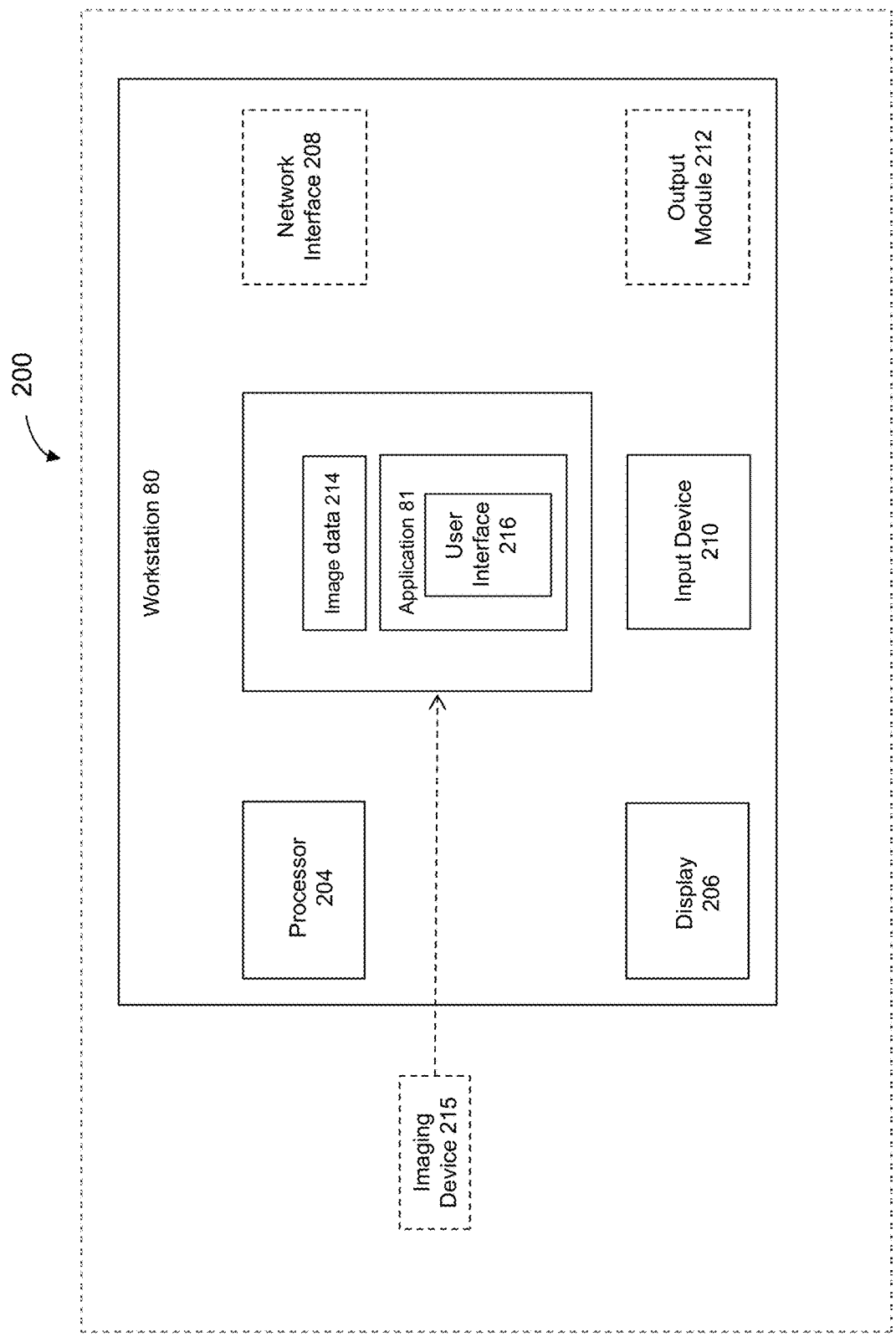
FIG. 2 is a schematic diagram of a system configured for use with the method of FIG. 1.

Reference is now made to FIG. 2, which is a schematic diagram of a system 200 configured for use with the method of FIG. 1 and as described herein above. System 200 may include a workstation 80, and optionally a fluoroscopic imaging device or fluoroscope 215. In some embodiments, workstation 80 may be coupled with fluoroscope 215, directly or indirectly, e.g., by wireless communication. Workstation 80 may include memory 202 (e.g., storage device), a processor 204, a display 206 and an input device 210. Processor or hardware processor 204 may include one or more hardware processors. Workstation 80 may optionally include an output module 212 and a network interface 208. Memory 202 may store an application 81 and image data 214. Application 81 may include instructions executable by processor 204, inter alia, for executing the method steps of FIG. 1 and as described herein above. Application 81 may further include a user interface 216. Image data 214 may include the 3D imaging such as a pre-operative CT scan, the F3DRs of the target area and/or any other fluoroscopic image data and/or one or more virtual fluoroscopy images. Processor 204 may be coupled with memory 202, display 206, input device 210, output module 212, network interface 208 and imaging device (e.g., fluoroscope 215). Workstation 80 may be a stationary computing device, such as a personal computer, or a portable computing device such as a tablet computer. Workstation 80 may embed a plurality of computer devices.

Memory 202 may include any non-transitory computer-readable storage media for storing data and/or software including instructions that are executable by processor 204 and which control the operation of workstation 80 and in some embodiments, may also control the operation of fluoroscope 215. Fluoroscope 215 may be used to capture a sequence of fluoroscopic images based on which the F3DR is generated. The two-dimensional fluoroscopic images in which the medical device is selected may be selected from the captured sequence of fluoroscopic images. In an embodiment, storage device or memory 202 may include one or more storage devices such as solid-state storage devices such as flash memory chips. Alternatively, or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 80.

Application 81 may, when executed by processor 204, cause display 206 to present user interface 216. User interface 216 may be configured to present to the user the F3DR, two-dimensional fluoroscopic images, images of the 3D imaging and virtual fluoroscopy image, as shown, for example, in the exemplary screen shots of FIGS. 3A-3F and 4A-4F. User interface 216 may be further configured to direct the user to select the target by, inter alia, identifying and marking the target in the displayed F3DR or any other fluoroscopic image data in accordance with the present disclosure.

Network interface 208 may be configured to connect to a network such as a local area network (LAN) consisting of a wired network and/or a wireless network, a wide area network (WAN), a wireless mobile network, a Bluetooth network, and/or the internet. Network interface 208 may be used to connect between workstation 80 and fluoroscope 215. Network interface 208 may be also used to receive image data 214. Input device 210 may be any device by means of which a user may interact with workstation 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

From the foregoing and with reference to the various figure drawings, those skilled in the art will appreciate that certain modifications can also be made to the present disclosure without departing from the scope of the same.

Detailed embodiments of the present disclosure are disclosed herein. However, the disclosed embodiments are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ the present disclosure in virtually any appropriately detailed structure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A system for identification and marking of a target in a body region of a patient, the system comprising:
   (i) a display;
   (ii) a computing device including a processor and a storage device, the storage device storing thereon instructions that when executed by the processor cause the computing device to:
   receive a sequence of fluoroscopic images of the body region about a plurality of angles relative to the body region while a medical device is positioned in a target area of the target in the body region of the patient;
   generate a Fluoroscopic Three-Dimensional Reconstruction (F3DR) of the body region based on the sequence of fluoroscopic images;
   receive an identification of the medical device in a first two-dimensional fluoroscopic image from the sequence of fluoroscopic images;
   receive a first identification of the target in the F3DR;
   determine a range of fluoroscopic slices of the F3DR for scrolling based on the identification of the target or the medical device;
   display a second fluoroscopic slice image from the determined range of fluoroscopic slices of the F3DR on the display;
   receive a second identification of the target in the second fluoroscopic slice image;
   determine an offset of the medical device with respect to the target based on the identification of the medical device and at least one of the first identification of the target or the second identification of the target; and
   register the F3DR to a computed tomography (CT) scan stored in the storage device.

2. The system of claim 1, wherein the storage device stores thereon further instructions that when executed by the processor cause the computing device to:
  determine a second range of fluoroscopic slices of the F3DR based on selection of the medical device prior to initial selection of the target.

3. The system of claim 1, wherein the storage device stores thereon further instructions that when executed by the processor cause the computing device to:
  receive the CT scan, wherein the CT scan is of the body region of the patient and includes a marking of the target;
  generate at least one virtual fluoroscopy image based on the CT scan, wherein the virtual fluoroscopy image includes the target and the marking of the target; and
  display the virtual fluoroscopy image.

4. The system of claim 1, wherein display of the second fluoroscopic slice image from the determined range of fluoroscopic slices of the F3DR on the display comprises displaying a series of different slices of the F3DR.

5. The system of claim 1, wherein display of the second fluoroscopic slice image from the determined range of fluoroscopic slices of the F3DR on the display comprises displaying a series of different slices at different capture angles.

6. The system of claim 1, wherein receiving the second identification of the target in the second fluoroscopic slice image comprises directing a user to identify and mark the target in two slices of the F3DR captured at two different angles.

7. The system of claim 1, wherein a thickness of a fluoroscopic slice from the determined range of fluoroscopic slices of the F3DR is reduced to achieve better resolution.

8. The system of claim 1, wherein the target comprises at least a portion of lungs and the medical device is configured to be navigated to the target through a luminal network of lungs.

9. The system of claim 1, wherein the storage device stores thereon further instructions that when executed by the processor cause the computing device to:
  receive a three-dimensional image data set of the body region of the patient, wherein the three-dimensional image data set includes a marking of the target; and
  displaying the three-dimensional image data set.

10. The system of claim 9, wherein the three-dimensional image data set is a CT or a magnetic resonance imaging (MRI) scan.

11. A method for marking of a target in a body region of a patient, the method comprising:
  receiving a sequence of fluoroscopic images of the body region while a medical device is positioned proximate a target in the body region of the patient;
  generating a Fluoroscopic Three-Dimensional Reconstruction (F3DR) of the body region based on the sequence of fluoroscopic images;
  receiving an identification of the medical device in a first two-dimensional fluoroscopic image from the sequence of fluoroscopic images;
  receiving a first identification of the target in the F3DR;
  determining a range of fluoroscopic slices of the F3DR for scrolling based on the identification of the target or the medical device;
  displaying a second fluoroscopic slice image from the determined range of fluoroscopic slices of the F3DR on a display;
  receiving a second identification of the target in the displayed second fluoroscopic slice image; and
  determining an offset of the medical device with respect to the target based on the identification of the medical device and at least one of the identification of the target or the second identification of the target.

12. The method of claim 11, further comprising:
  determining the range of fluoroscopic slices of the F3DR based on the identification of the medical device prior to identification of the target.

13. The method of claim 11, further comprising:
  receiving a computed tomography (CT) scan of the body region of the patient, wherein the CT scan includes a marking of the target;
  generating at least one virtual fluoroscopy image based on the CT scan, wherein the virtual fluoroscopy image includes the target and the marking of the target; and
  displaying the virtual fluoroscopy image on the display.

14. The method of claim 11, wherein displaying the second fluoroscopic slice image from the determined range of fluoroscopic slices of the F3DR on the display comprises displaying a series of slices of the F3DR.

15. The method of claim 11, wherein the displaying the second fluoroscopic slice image from of the determined range of slices of the F3DR on the display comprises displaying a series of slices of the F3DR at different capture angles.

16. The method of claim 11, wherein receiving the second identification of the target in the second fluoroscopic slice image comprises directing a user to identify and mark the target in two fluoroscopic slices of the F3DR captured at two different angles.

17. The method of claim 11 wherein a thickness of the fluoroscopic slices from the determined range of fluoroscopic slices of the F3DR is reduced to achieve better resolution.

18. The method of claim 11, wherein the target comprises at least a portion of lungs and the medical device is configured to be navigated to the target through a luminal network of lungs.

19. The method of claim 11, further comprising:
  receiving a three-dimensional image data set of the body region of the patient, wherein the three-dimensional image data set includes a marking of the target; and
  displaying the three-dimensional image data set.

20. The method of claim 19, wherein the method is used during a medical procedure, and wherein the three-dimensional image data set is a pre-operative imaging which was used in a planning phase of the medical procedure.

* * * * *